United States Patent
Benoit et al.

(10) Patent No.: US 6,624,154 B1
(45) Date of Patent: Sep. 23, 2003

(54) COMPOSITIONS AND METHODS FOR TREATMENT OF HYPERPROLIFERATIVE DISEASES

(75) Inventors: Gérard Benoit, Monrsouir (FR); Hinrich Gronemeyer, Oberkirch (DE); Michel Lanotte, Paris (FR); Marco Gottardis, Princeton, NJ (US)

(73) Assignees: Bristol-Myers Squibb Company, Princeton, NJ (US); Institut National de la Sante et de la Recherche Medicale, Paris (FR); Centre National de la Recherche Scientifique, Paris (FR); Universite Louis Pasteur, Strasbourg (FR)

( * ) Notice: Subject to any disclaimer, the term of this patent is extended or adjusted under 35 U.S.C. 154(b) by 0 days.

(21) Appl. No.: 09/556,675

(22) Filed: Apr. 21, 2000

Related U.S. Application Data

(60) Provisional application No. 60/130,649, filed on Apr. 23, 1999.

(51) Int. Cl.[7] .......................... A01N 45/00; A61K 38/19
(52) U.S. Cl. ...................... 514/168; 424/85.1; 424/194; 424/15; 424/21
(58) Field of Search ...................... 514/168; 424/155.1, 424/198.1, 85.1; 435/194, 21, 15

(56) References Cited

U.S. PATENT DOCUMENTS

| | | | | |
|---|---|---|---|---|
| 5,455,265 | A | * 10/1995 | Chandraratna | 51/448 |
| 5,559,248 | A | 9/1996 | Starrett, Jr. et al. | 549/79 |
| 5,618,839 | A | 4/1997 | Starrett, Jr. et al. | 514/513 |
| 5,624,957 | A | 4/1997 | Swann et al. | 514/535 |
| 5,849,923 | A | 12/1998 | Starrett, Jr. et al. | 546/340 |

FOREIGN PATENT DOCUMENTS

| | | |
|---|---|---|
| WO | WO 94/26100 | 11/1994 |
| WO | WO 98/46228 | 10/1998 |
| WO | WO 98/47861 | 10/1998 |

OTHER PUBLICATIONS

Kurie et al. 1993, Differentiation, vol. 54, pp. 115–122. Cooperation between retinoic acid and phorbol esters enhances human teratocarcinoma differentiation.*

Miyauchi J. Leuk Lymphoma 1999, vol. 33, pp. 267–280. All–trans retinoic acid and hemtopoeitic growth factors regulating the grwoth and differentiation of blast progenitors in acute promyelocytic leukemia.*

Nazareth LV, Weigel NL J Biol chem 1996, 271 (33):19900–19907.*

Tsurumi H, Tojo A, Takahashi T, Moriwaki H, Asano S, and Muto Y Internal Med 1993, 32(8): 648–650.*

Alcalay, M. et al., "Translocation breakpoint of acute promyelocytic leukemia lies within the retinoic acid receptor α locus," Proc. Natl. Acad. Sci. USA 88:1977–1981 (1991).

Benbrook, D.M. et al., "Biologically Active Heteroarotinoids Exhibiting Anticancer Activity and Decreased Toxicity," J. Med. Chem. 40:3567–3583 (1997).

Boehm, M.F. et al., "Synthesis and Structure–Activity Relationships of Novel Retinoid X Receptor–Selective Retinoids," J. Med. Chem. 37:2930–2941 (1994).

Boehm, M.F. et al., "Design and Synthesis of Potent Retinoid X Receptor Selective Ligands that Induce Apoptosis in Leukemia Cells," J. Med. Chem. 38:3146–3155 (1995).

Bollag, W. and Holdener, E.E., "Retinoids in cancer prevention and therapy," Ann. Oncol. 3:513–526 (1992).

Bonhomme, L. et al., "Topical treatment of epidemic Kaposi's sarcoma with all–trans–retinoic acid," Ann. Oncol. 2:234–235 (1991).

Brindle, P.K. and Montminy, M.R., "The CREB family of transcription activators," Curr. Opin. Genet. Dev. 2:199–204 (1992).

Bugge, T.H. et al., "RXRα, a promiscuous partner of retinoic acid and thyroid hormone receptors," EMBO J. 11:1409–1418 (1992).

Castaigne, S. et al., "All–Trans Retinoic Acid as a Differentiation Therapy for Acute Promyelocytic Leukemia. I. Clinical Results," Blood 76:1704–1709 (1990).

Chambon, P. "The retinoid signaling pathway: molecular and genetic analyses," Semin. Cell Biol. 5:115–125 (1994).

Chambon, P. "A decade of molecular biology of retinoic acid receptors," FASEB J. 10:940–954 (1996).

Chen, G.–Q. et al., "In Vitro Studies on Cellular and Molecular Mechanisms of Arsenic Trioxide ($As_2O_3$) in the Treatment of Acute Promyelocytic Leukemia: $As_2O_3$ Induces $NB_4$ Cell Apoptosis with Downregulation of Bcl–2 Expression and Modulation of PML–RARα/PML Proteins," Blood 88:1052–1061 (1996).

Chen, J.–Y. et al., "RAR–specific agonist/antagonist which dissociate transactivation and AP1 transrepression inhibit anchorage–independent cell proliferation," EMBO J. 14:1187–1197 (1995).

Chen, J.–Y. et al., "Two distinct actions of retinoid–receptor ligands," Nature 382:819–822 (1996).

Chen, Z. et al., "The Retinoic Acid Alpha Receptor Gene is Frequently Disrupted in its 5' Part in Chinese Patients with Acute Promyelocytic Leukemia," Leukemia 5:288–292 (1991).

Chen, Z.–P. et al., "Ligand– And DNA–induced Dissociation of RXR Tetramers," J. Mol. Biol. 275:55–65 (Jan. 1998).

Chiesa, F. et al., "Prevention of Local Relapses and New Localisations of Oral Leukoplakias with the Synthetic Retinoid Fenretinide (4–HPR). Preliminary Results," Eur. J. Cancer B. Oral Oncol. 28:97–102 (1992).

(List continued on next page.)

Primary Examiner—Prema Mertz
(74) Attorney, Agent, or Firm—Sterne, Kessler, Goldstein & Fox, P.L.L.C.

(57) ABSTRACT

The invention relates to compositions comprising a retinoid X receptor agonist and an agent capable of activating protein kinase A. The invention also relates to methods of treating hyperproliferative diseases by administering a retinoid X receptor agonist and an agent capable of activating protein kinase A.

39 Claims, 8 Drawing Sheets

OTHER PUBLICATIONS

Chomienne, C. et al., "All–Trans Retinoic Acid in Acute Promyelocytic Leukemias. II. In Vitro Studies: Structure–Function Relationship," *Blood* 76:1710–1717 (1990).

Chomienne, C. et al., "All–trans Retinoic Acid Modulates the Retinoic Acid Receptor–α in Promyelocytic Cells," *J. Clin. Invest.* 88:2150–2154 (1991).

Chomienne, C. et al., "Retinoid differentiation therapy in promyelocytic leukemia," *FASEB J.* 10:1025–1030 (1996).

Conti, M. et al., "Recent Progress in Understanding the Hormonal Regulation of Phosphodiesterases," *Endocrine Reviews* 16:370–389 (1995).

Costa, A. et al., "Prospects of Chemoprevention of Human Cancers with the Synthetic Retinoid Fenretinide," *Cancer Res.* 54(*Suppl. 7*):2032s–2037s (1994).

Daniel, P.B. et al., "Cyclic AMP Signaling and Gene Regulation," *Ann. Rev. Nutr.* 18:353–383 (Jul. 1998).

Dey, A., et al. "Ligand–Dependent Occupancy of the Retinoic Acid Receptor β2 Promoter In Vivo," *Mol. Cell. Biol.* 14:8191–8201 (1994).

Dollé, P. et al., "Developmental expression of murine retinoid X receptor (RXR) genes," *Mech. Dev.* 45:91–104 (1994).

Doucas, V. et al., "The PML–retinoic acid receptor α translocation converts the receptor from an inhibitor to a retinoic acid–dependent activator of transcription factor AP–1," *Proc. Natl. Acad. Sci. USA* 90:9345–9349 (1993).

Duprez, E. et al., "A Retinoid Acid 'Resistant' t(15;17) Acute Promyelocytic Leukemia Cell Line: Isolation, Morphological, Immunological, and Molecular Features," *Leukemia* 6:1281–1287 (1992).

Duprez, E. et al., "cAMP signalling is decisive for recovery of nuclear bodies (PODs) during maturation of RA–resistant t(15;17) promyelocytic leukemia NB4 cells expressing PML–RARα," *Oncogene* 12:2451–2459 (1996).

Durand, B. et al., "All–Trans and 9–Cis Retinoic Acid Induction of CRABPII Transcription is Mediated by RAR–RXR Heterodimers Bound to DR1 and DR2 Repeated Motifs," *Cell* 71:73–85 (1992).

Dyck, J.A. et al., "A Novel Macromolecular Structure is a Target of the Promyelocyte–Retinoic Acid Receptor Oncoprotein," *Cell* 76:333–343 (1994).

Fenaux, P. et al., "Acute Promyelocytic Leukemia: Biology and Treatment," *Semin. Oncol.* 24:92–102 (1997).

Forman, B.M. et al., "Unique Response Pathways are Established by Allosteric Interactions Among Nuclear Hormone Receptors," *Cell* 81:541–550 (1995).

de Gentile, A. et al., "Induction of High–Affinity GM–CSF Receptor during All–Trans Retinoic Acid Treatment of Acute Promyelocyte Leukemia," *Leukemia* 8:1758–1762 (1994).

Green, S. "Nuclear Hormone Receptors. Promiscuous liasons," *Nature* 361:590–591 (1993).

Grignani, F. et al., "The Acute Promyelocytic Leukemia–Specific PML–RARα Fusion Protein Inhibits Differentiation and Promotes Survival of Myeloid Precursor Cells," *Cell* 74:423–431 (1993).

Gudas, L.J. et al., "Cellular Biology and Biochemistry of the Retinoids," in *The Retinoids*, 2nd ed., Sporn, M.B., eds., et al., New York: Raven Press pp. 443–520 (1994).

Halachmi, S. et al., "Estrogen Receptor–Associated Proteins: Possible Mediators of Hormone–Induced Transcription," *Science* 264:1455–1458 (1994).

Hodgson, J. "Protein Design: Rules, Empiricism, & Nature," *Biotechnology* 8:1245–1247 (1990).

Hodgson, J. "Carbohydrate–Based Therapeutics," *Biotechnology* 9:609–611, 613 (1991).

Hong, W.K. et al., "13–cis–Retinoic Acid in the Treatment of Oral Leukoplakia," *N. Engl. J. Med.* 315:1501–1505 (1986).

Hong, W.K. et al., "Prevention of Second Primary Tumors with Isotretinoin in Squamos–Cell Carcinoma of the Head and Neck," *N. Engl. J. Med.* 323:795–801 (1990).

Horn, V. et al., "RAR and RXR selective ligands cooperatively induce apoptosis and neuronal differentiation in P19 embryonal carcinoma cells," *FASEB J.* 10:1071–1077 (1996).

Huang, M.–E. et al., "Use of All–Trans Retinoic Acid in the Treatment of Acute Promyelocytic Leukemia," *Blood* 72:567–572 (1988).

Imaizumi, M. "Mutations in the E–Domain of RARα Portion of the PML/RARα Chimeric Gene May Confer Clinical Resistance to All–trans Retinoic Acid in Acute Promyelocytic Leukemia," *Blood* 92:374–382 (Jul. 1998).

Kastner, P. et al., "Structure, localization and transcriptional properties of two classes of retinoic acid receptor α fusion proteins in acute promyelocytic leukemia (APL): structural similarities with a new family of oncoproteins," *EMBO J.* 11:629–642 (1992).

Kastner, P. and Chambon, P., "Role of Nuclear Retinoic Acid Receptors in the Regulation of Gene Expression," in *Vitamin A in health and Disease*, R. Blomhoff, ed., Marcel Dekker, New York, pp. 189–238 (1994).

Kastner, P. et al., "Nonsteroid Nuclear Receptors: What Are Genetic Studies Telling us about Their Role in Real Life?" *Cell* 83:859–869 (1995).

Kastner, P. et al., "Abnormal spermatogenesis in RXRβ mutant mice," *Genes & Dev.* 10:80–92 (1996).

Katayama, N. et al., "Granulocyte Colony–Stimulating Factor and Its Receptor in Acute Promyelocytic Leukemia," *Am. J. Hematol.* 58:31–35 (May 1998).

Kersten, S. et al., "Individual Subunits of Heterodimers Comprised of Retinoic Acid and Retinoid X Receptors Interact with Their Ligands Independently," *Biochem.* 35:3816–3824 (1996).

Kishimoto, T. et al., "Interleukin–6 and Its Receptor: A Paradigm for Cytokines," *Science* 258:593–597 (1992).

Kitamura, K. et al., "Mutant AF–2 domain of PML–RARα in retinoic acid–resistant NB4 cells: differentiation induced by RA is triggered directly through PML–RARα and its down–regulation in acute promyelocytic leukemia," *Leukemia* 11:1950–1956 (1997).

Kliewer, S.A. et al., "Retinoid X receptor interacts with nuclear receptors in retinoic acid, thyroid hormone and vitamin $D_3$ signalling," *Nature* 355:446–449 (1992).

Koken, M.H.M. et al., "The t(15;17) translocation alters a nuclear body in a retinoic acid–reversible fashion," *EMBO J.* 13:1073–1083 (1994).

Kraemer, K.H. et al., "Prevention of Skin Cancer in Xeroderma Pigmentosum with the Use of Oral Isotretinoin," *N. Engl. J. Med.* 318:1633–1637 (1988).

Kurokawa, R. et al., "Regulation of retinoid signalling by receptor polarity and allosteric control of ligand binding," *Nature* 371:528–531 (1994).

Lanotte, M. et al., "NB4, a Maturation Inducible Cell Line with t(15;17) Marker Isolated From a Human Acute Promyelocytic Leukemia (M3)," *Blood* 77:1080–1086 (1991).

Laudet, V. and Stehelin, D., "Flexible friends. Nuclear receptors of the thyroid hormone receptor and retinoic acid receptor subfamily bind some DNA response elements in combination with auxillary proteins, which turn out to be also nuclear receptors," *Curr. Biol.* 2:293–295 (1992).

Lee, K.A.W. and Masson, N., "Transcriptional regulation by CREB and its relatives," *Biochim. Biophys. Acta* 1174:221–233 (1993).

Lehmann, J.M. et al., "Retinoids Selective for Retinoid X Receptor Response Pathways," *Science* 258: 1944–1946 (1992).

Leid, M. et al., "Purification, Cloning, and RXR Identity of the HeLa Cell Factor with Which RAR or TR Heterodimerizes to Bind Target Sequences Efficiently," *Cell* 68:377–395 (1992).

Leid, M. et al., "Multiplicity generates diversity in the retinoic acid signalling pathways," *TIBS* 17:427–433 (1992).

Li, C. et al., "Coexpression of nuclear receptor partners increases their solubility and biological activities," *Proc. Natl. Acad. Sci. USA* 94:2278–2283 (1997).

Linney, E. "Retinoic Acid Receptors: Transcription Factors Modulating Gene Regulation, Development, and Differentiation," *Curr. Topics Dev. Biol.* 27:309–350 (1992).

Lippman, S.M. et al., "13–cis–Retinoic Acid and Interferon α–2a: Effective Combination Therapy for Advanced Squamos Cell Carcinoma of the Skin," *J. Natl. Cancer Inst.* 84:235–241 (1992).

Lippman, S.M. et al., "13–cis–Retinoic Acid Plus Interferon α–2: Highly Active Systemic Therapy for Squamos Cell Carcinoma of the Cervix," *J. Natl. Cancer Inst.* 84:241–245 (1992).

Lo Coco, F. et al., "Molecular Evaluation of Response to All–Trans–Retinoic Acid Therapy in Patients with Acute Promyelocytic Leukemia," *Blood* 77:1657–1659 (1991).

Mader, S. et al., "Multiple Parameters Control the Selectivity of Nuclear Receptors for Their Response Elements. Selectivity and Promiscuity in Response Element Recognition by Retinoic Acid Receptors and Retinoid X Receptors," *J. Biol. Chem.* 268:591–600 (1993).

Mangelsdorf, D.J. et al., "The Nuclear Receptor Superfamily: The Second Decade," *Cell* 83:835–839 (1995).

Mangelsdorf, D.J. and Evans R.M., "The RXR Heterodimers and Orphan Receptors," *Cell* 83:841–850 (1995).

Marks, M.S. et al., "H–2RIIBP (RXRβ) heterodimerization provides a mechanism for combinatorial diversity in the regulation of retinoic acid and thyroid hormone responsive genes," *EMBO J.* 11:1419–1435 (1992).

Mascrez, B. et al., "The RXRα ligand–dependent activation function 2 (AF–2) is important for mouse development," *Development* 125:4691–4707 (Dec. 1998).

Miller, V.A. et al., "Initial Clinical Trial of a Selective Retinoid X Receptor Ligand, LGD1069," *J. Clin. Oncol.* 15:790–795 (1997).

Mu, Z.–M. et al., "PML, a Growth Suppressor Disrupted in Acute Promyelocytic Leukemia," *Mol. Cell. Biol.* 14:6858–6867 (1994).

Mukherjee, R. et al., "Sensitization of diabetic and obese mice to insulin by retinoid X receptor agonists," *Nature* 386:407–410 (1997).

Nagpal, S. et al., "Promoter Context– and Response Element– Dependent Specificity of the Transcriptional Activation and Modulating Functions of Retinoic Acid Receptors," *Cell* 70:1007–1019 (1992).

Nagy, L. et al., "Activation of Retinoid X Receptors Induces Apoptosis in HL–60 Cell Lines," *Mol. Cell. Biol.* 15:3540–3551 (1995).

Perez, A. et al., "PMLRAR homodimers: distinct DNA binding properties and heteromeric interactions with RXR," *EMBO J.* 12:3171–3182 (1993).

Roy, B. et al., "Synergistic Activation of Retinoic Acid (RA)–Responsive Genes and Induction of Embryonal Carcinoma Cell Differentiation by an RA Receptor α (RAR α)–, RAR β–, or RAR γ–Selective Ligand in Combination with a Retinoid X Receptor–Specific Ligand," *Mol. Cell. Biol.* 15:6481–6487 (1995).

Ruchaud, S. et al., "Two distinctly regulated events, priming and triggering, during retinoid–induced maturation and resistance of NB4 promyelocytic leukemia cell line," *Proc. Natl. Acad. Sci. USA* 91:8428–8432 (1994).

Shao, W. et al., "A Retinoid–Resistant Acute Promyelocytic Leukemia Subclone Expresses a Dominant Negative PML–RARα Mutation," *Blood* 89:4282–4289 (1997).

Soignet, S.L. et al., "Complete Remission After Treatment of Acute Promyelocytic Leukemia with Arsenic Trioxide," *N. Engl. J. Med.* 339:1341–1348 (Nov. 1998).

Sun, S.–Y. et al., "Differential Effects of Synthetic Nuclear Retinoid Receptor–selective Retinoids on the Growth of Human Non–Small Cell Lung Carcinoma Cells," *Cancer Res.* 57:4931–4939 (1997).

Sunaga, S. et al., "Myeloid differentiation is impaired in transgenic mice with targeted expression of a dominant negative form of retinoid X receptor β," *Br. J. Haematol.* 96:19–30 (1997).

Tkatch, L.S. et al., "Modulation of human G–CSF receptor mRNA and protein in normal and leukemic myeloid cells by G–CSF and retinoic acid," *J. Leukoc. Biol.* 57:964–971 (1995).

Tong, J.–H. et al., "Expression patterns of the JEM–1 gene in normal and tumor cells: ubiquity contrasting with a faint, but retinoid–induced, mRNA expression in promyelocytic NB4 cells," *Leukemia* 12:1733–1740 (Nov. 1998).

Usuki, K. et al., "Administration of granulocyte colony–stimulating factor during remission induction therapy with all–trans retinoic acid for acute promyelocytic leukemia," *Intl. J. Hematol.* 64:213–219 (1996).

Verma, A.K., "Inhibition of Both Stage I and Stage II Mouse Skin Tumour Promotion by Retinoic Acid and the Dependence of Inhibition of Tumor Promotion on the Duration of Retinoic Acid Treatment," *Cancer Res.* 47:5097–5101 (1987).

Vivat, V. et al., "A mutation mimicking ligand–induced conformational change yields a constitutive RXR that senses allosteric effects in heterodimers," *EMBO J.* 16:5697–5709 (1997).

Warrell, R.P. et al., "Differentiation Therapy of Acute Promyelocytic Leukemia with Tretinoin (All–Trans–Retinoic Acid)," *N. Engl. J. Med.* 324:1385–1393 (1991).

Warrell, R.P. et al., "Acute Promyelocytic Leukemia," *N. Engl. J. Med.* 329:177–189 (1993).

Weigel, N.L., "Steroid hormone receptors and their regulation by phosphorylation," *Biochem. J.* 319:657–667 (1996).

Weis, K. et al., "Retinoic Acid Regulates Aberrant Nuclear Localization of PML–RARα in Acute Promyelocytic Leukemia Cells," *Cell* 76:345–356 (1994).

Yu, V.C. et al., "RXRβ: A Coregulator That Enhances Binding of Retinoic Acid, Thyroid Hormone, and Vitamin D Receptors to Their Cognate Response Elements," *Cell* 67:1251–1266 (1991).

Yu, V.C. et al., "Transcriptional regulation by the nuclear receptor superfamily," *Curr. Opin. Biotech.* 3:597–602 (1992).

Zhang, X.–K. et al., "Retinoid X receptor is an auxiliary protein for thyroid hormone and retinoic acid receptors," *Nature* 355:441–446 (1992).

\* cited by examiner

COMPOSITIONS AND METHODS FOR TREATMENT OF HYPERPROLIFERATIVE DISEASES

The present application claims benefit of the filing date of U.S. application Ser. No. 60/130,649, filed Apr. 23, 1999, which disclosure is incorporated herein in entirety by reference.

BACKGROUND OF THE INVENTION

1. Field of the Invention

The invention relates to compositions comprising a retinoid X receptor agonist and an agent capable of activating protein kinase A. The invention also relates to methods of treating hyperproliferative diseases by administering a retinoid X receptor agonist and an agent capable of activating protein kinase A.

2. Related Art

Retinoids and Receptors

A number of studies have demonstrated that retinoids (vitamin A derivatives) are essential for normal growth, vision, tissue homeostasis, reproduction and overall survival (for reviews and references, see Sporn et al., *The Retinoids*, Vols. 1 and 2, Sporn et al., eds., Academic Press, Orlando, Fla. (1984)).

Except for those involved in visual perception (Wald, G. et al., *Science* 162:230–239 (1968)), the molecular mechanisms underlying the highly diverse effects of retinoids have until recently remained obscure. The discovery of nuclear receptors for retinoic acid (RA) (Petkovich et al., *Nature* 330:444–450 (1987); Giguère et al., *Nature* 330:624–629 (1987)) has greatly advanced the understanding of how the retinoids may exert their pleiotropic effects (Leid, M., et al., *TIBS* 17:427–433 (1992); Linney, E., *Current Topics in Dev. Biol.* 27:309–350 (1992)). It is thought that the effects of the RA signal are mediated through two families of receptors—the RAR family and RXR family—which belong to the superfamily of ligand-inducible transcriptional regulatory factors that include steroid/thyroid hormone and vitamin D3 receptors (for reviews, see Leid, M., et al., *TIBS* 17:427–433 (1992); Chambon, P., *Semin. Cell Biol.* 5:115–125 (1994); Chambon, P., *FASEB J.* 10:940–954 (1996); Giguere, V., *Endocrinol. Rev.* 15:61–79 (1994); Mangelsdorf, D. J., and Evans, R. M., *Cell* 83:841–850 (1995); Gronemeyer, H., and Laudet, V., *Protein Profile* 2:1173–1236 (1995)).

Receptors belonging to the retinoic acid receptor family (RARα, β and γ and their isoforms) are activated by both all-trans- and 9-cis-RA (Leid, M., et al., *TIBS* 17:427–433 (1992); Chambon, P., *Semin. Cell Biol.* 5:115–125 (1994); Dolle, P., et al., *Mech. Dev.* 45:91–104 (1994)). Unlike the RARs, members of the retinoid X receptor family (RXRα, β and γ) are activated exclusively by 9-cis-RA (Chambon, P., *Semin. Cell Biol.* 5:115–125 (1994); Dollé, P., et al., *Mech. Dev.* 45:91–104 (1994); Linney, E., *Current Topics in Dev. Biol.* 27:309–350 (1992); Leid, M., et al., *TIBS* 17:427–433 (1992); Kastner et al., In: *Vitamin A in Health and Disease*, R. Blomhoff, ed., Marcel Dekker, New York (1993)).

Nuclear receptors (NRs) are members of a superfamily of ligand-inducible regulatory factors that include receptors for steroid hormones, thyroid hormones, vitamin D3 and retinoids (Leid, M., et al., *Trends Biochem. Sci.* 17:427–433 (1992); Leid, M., et al., *Cell* 68:377–395 (1992); and Linney, E. *Curr. Top. Dev. Biol.*, 27:309–350 (1992)). NRs exhibit a modular structure which reflects the existence of several autonomous functional domains. Based on amino acid sequence similarity between the chicken estrogen receptor, the human estrogen and glucocorticoid receptors, and the v-erb-A oncogene, Krust, A., et al. (*EMBO J.* 5:891–897 (1986)) defined six regions—A, B, C, D, E and F—which display different degrees of evolutionary conservation among various members of the nuclear receptor superfamily. The highly conserved region C contains two zinc fingers and corresponds to the core of the DNA-binding domain (DBD), which is responsible for specific recognition of the cognate response elements. Region E is functionally complex, since in addition to the ligand-binding domain (LBD), it contains a ligand-dependent activation function (AF-2) and a dimerization interface. An autonomous transcriptional activation function (AF-1) is present in the non-conserved N-terminal A/B regions of the steroid receptors. Interestingly, both AF-1 and AF-2 of steroid receptors exhibit differential transcriptional activation properties which appear to be both cell type and promoter context specific (Gronemeyer, H., *Annu. Rev. Genet.* 25:89–123 (1991)).

It has been shown that activation of RA-responsive promoters likely occurs through RAR/RXR heterodimers rather than through homodimers (Yu, V.C., et al., *Cell* 67:1251–1266 (1991); Leid, M., et al., *Cell* 68:377–395 (1992b); Durand et al., *Cell* 71:73–85 (1992); Nagpal, S., et al., *Cell* 70:1007–1019 (1992); Zhang, X. K., et al., *Nature* 355, 441–446 (1992); Kliewer et al., *Nature* 355:446–449 (1992); Bugge et al., *EMBO J.* 11:1409–1418 (1992); Marks et al., *EMBO J.* 11:1419–1435 (1992); Yu, V. C. et al., *Cur. Op. Biotech.* 3:597–602 (1992); Leid, M., et al., *TIBS* 17:427–433 (1992); Laudet and Stehelin, *Curr. Biol.* 2:293–295 (1992); Green, S., *Nature* 361:590–591 (1993)). The RXR portion of these heterodimers has been proposed to be silent in retinoid-induced signaling (Kurokawa, R., et al., *Nature* 371:528–531 (1994); Forman, B. M., et al., *Cell* 81:541–550 (1995); Mangelsdorf, D. J., and Evans, R. M., *Cell* 83:835–850 (1995); Vivat, V. et al., *EMBO J.* 16:5697–5709 (1997)) but conflicting results have been reported as far as the ligand-binding ability of RXR in heterodimers is concerned (Kurokawa, R., et al., *Nature* 371:528–531 (1994); Chen, J.-Y. et al., *Nature* 382:819–822 (1996); Kersten, S. et al., *Biochem.* 35:3 816–3824 (1996); Chen, Z. et al., *J. Mol. Bio.* 275:55–65 (1998); Li, C. et al., *Proc. Natl. Acad. Sci. USA* 94:2278–2283 (1997). The results of these and of genetic studies strongly suggest that RAR/RXR heterodimers are indeed functional units that transduce the RA signal in vivo (Chambon, P., *Semin. Cell Biol.* 5:115–125 (1994); Kastner, P. et al., *Cell* 83:859–869 (1995); Mascrez, B. el al., *Development* 125:4691–4707 (1998)). Thus, the basis for the highly pleiotropic effect of retinoids may reside, at least in part, in the control of different subsets of retinoid-responsive promoters by cell-specifically expressed heterodimeric combinations of RAR/RXR subtypes (and isoforms), whose activity may be in turn regulated by cell-specific levels of all-trans- and 9-cis-RA (Leid, M., et al., *TIBS* 17:427–433 (1992)).

The RXR receptors may also be involved in RA-independent signaling. For example, the observation of aberrant lipid metabolism in the Sertoli cells of RXRβ+ mutant animals suggests that functional interactions may also occur between RXRβ and the peroxisomal proliferator-activated receptor signaling pathway (WO 94/26100; Kastner, P., et al., *Genes & Dev.* 10:80–92 (1996)).

Therapeutic Uses of Retinoids

Overview

As retinoic acid is known to regulate the proliferative and differentiative capacities of several mammalian cell types (Gudas, L. J., et al., In: *THE RETINOIDS*, 2nd ed., Sporn, M. B., et al., eds., New York: Raven Press, pp. 443–520 (1994)), retinoids are used in a variety of chemopreventive and chemotherapeutic settings. The prevention of oral, skin, head and neck cancers in patients at risk for these tumors has been reported (Hong, W. K., et al., N. *Engl. J. Med.* 315:1501–1505 (1986); Hong, W. K., et al., N. *Engl. J. Med.* 323:795–801 (1990); Kraemer, K. H., et al., *N. Engl. J. Med.* 318:1633–1637 (1988); Bollag, W., et al., *Ann. Oncol.* 3:513–526 (1992); Chiesa, F., et al., Eur. *J. Cancer B. Oral Oncol.* 28:97–102 (1992); Costa, A., et al., *Cancer Res.* 54:Supp. 7,2032–2037(1994)). Retinoids have also been used to treat squamous cell carcinoma of the cervix and the skin (Verma, A. K., *Cancer Res.* 47:5097–5101 (1987); Lippman S. M., et al., *J. Natl Cancer Inst.* 84:235–241 (1992); Lippman S. M., et al., *J. Natl Cancer Inst.* 84:241–245 (1992)) and Kaposi's sarcoma (Bonhomme, L., et al., *Ann. Oncol.* 2:234–235 (1991)), and have found significant use in the therapy of acute promyelocytic leukemia (Huang, M. E., et al., *Blood* 72:567–572 (1988); Castaigne, S., et al., *Blood* 76:1704–1709 (1990); Chomienne, C., et al., *Blood* 76:1710–1717 (1990); Chomienne, C., et al.,*J. Clin. Invest.* 88:2150–2154 (1991); Chen Z., et al.,*Leukemia* 5:288–292 (1991); Lo Coco, F., el al., *Blood* 77:1657–1659 (1991); Warrell, R. P., et al., *N. Engl. J. Med.* 324:1385–1393 (1991); Chomienne, C., et al., *FASEB J.* 10:1025–1030 (1996)). Retinoids are also used to treat hyperproliferative skin disorders such as psoriasis. 13-cis retinoic acid (isotretinoin) is commonly used as a dermatologic drug.

Acute Promyelocytic Leukemia (APL)

A balanced chromosomal translocation, t(15; 17), has been identified in most acute promyelocytic leukemia (APL) cells (Larson, A. R., et al.,*Am. J. Med.* 76:827–841 (1984)). The breakpoint for this translocation occurs within the second intron of the RARα gene (Alcalay, M. D., et al., *Proc. Natl. Acad. Sci. USA* 88:1977–1981 (1991); Chang, K. S., el al.,*Leukemia* 5:200–204 (1991); Chen, S., et al.,*Blood* 78:2696–2701 (1991) and within two loci of the gene encoding the putative zinc finger transcription factor PML (Goddard, A., et al., *Science* 254:1371–1374(1991)). This reciprocal t(15;17) translocation leads to the generation of a PML-RARα fusion protein which is co-expressed with PML and RARα in APL cells (see Warrell, R. P., et al., *N. Engl. J. Med.* 329:177–189 (1993); Grignáni, F., et al., *Blood* 83:10–25 (1994); Lavau, C., and Dejean, A., *Leukemia* 8:1615–1621 (1994); de Thé, H., *FASEB J.* 10:955–960 (1996)). The PML-RARα fusion is apparently responsible for the differentiation block at the promyelocytic stage, since (i) it is observed in nearly all APL patients (Warrell, R. P., et al., *N. Engl. J. Med.* 329:177–189 (1993); Grignáni, F., el al., *Blood* 83:10–25 (1994); Lavau, C., and Dejean, A., *Leukemia* 8:1615–1621 (1994)), (ii) it inhibits myeloid differentiation when overexpressed in U937 or HL60 myeloblastic leukemia cells (Grignani, F., el al., *Cell* 74:423–431 (1993)), and (iii) complete clinical remission due to differentiation of the leukemic cells to mature granulocytes upon treatment with all-trans retinoic acid (ATRA) is tightly linked to PML-RARα expression (Warrell, R. P., et al., *N. Engl. J. Med.* 324:1385–1393 (1991); Lo Coco, R., et al., *Blood* 77:1657–1659 (1991); Chomienne, C., et al., *FASEB J.* 10:1025–1030 (1996)). Multiple studies have addressed the possible impact of PML-RARα fusion protein formation on cell proliferation (Mu, X.M., et al., *Mol. Cell. Biol.* 14:6858–6867 (1994)) and apoptosis (Grignani, F., et al., *Cell* 74:423–431 (1993)), AP1 transrepression (Doucas, V., et al.,*Proc. Natl. Acad. Sci. USA* 90:9345–9349(1993)), and vitamin D3 signaling (Perez, A., et al., *EMBO J.* 12:3171–3182 (1993)), but the mechanism(s) by which PML-RARα blocks myeloid cell maturation has remained elusive. Consistent with the aberrant nuclear compartmentalization of PML-RARα, which adopts the "PML-type" location upon RA treatment (Dyck, J. A., et al., *Cell* 76:333–343 (1994); Weis, K., et al., *Cell* 76:345–358 (1994); Koken, M. H., et al., *EMBO J.* 13:1073–1083 (1994)), the currently prevailing hypothesis is that PML-RARα possesses altered transcriptional properties compared to PML or RARα and/or may act in a dominant-negative manner (Perez, A., et al.,*EMBO J.* 12:3171–3182 (1993); de The, H., et al., *Cell* 66:675–684 (1991); Kastner, P., et al., *EMBO J.* 11:629–642 (1992)).

Acute promyelocytic leukemia (APL) is the prototype of a cancer treated by differentiation therapy using ATRA (Fenaux, P. et al., *Semin Oncol.* 24:92–102 (1997)). However, adjuvant chemotherapy which is required to improve tumor cell remission bears the inherent risk of therapy-induced ATRA resistance due to, for example, mutation oft he PML-RARα ligand binding domain. Such mutations are indeed frequently observed in relapsed patients (Imaizumi, M. et al., *Blood* 92:374–382 (1998)) and ATRA-resistant cell lines (Ruchaud, S. et al., *Proc. Natl. Acad. Sci. U.S.A.* 91:8428–8432 (1994); Shao, W. et al., *Blood* 89:4282–4289 (1997); Kizaki, M. et al., *Blood* 88:1824–1833 (1996); Robertson, K. A. et al., *Blood* 80:1885–1889 (1992); Kitamura, K. et al., *Leukemia* 11:1950–1956 (1997)).

Breast Cancer

Despite earlier detection and a lower size oft he primary tumors at the time of diagnosis (Nystrom, L. et al., Lancet 341:973–978 (1993); Fletcher, S. W. et al., *J. Natl. Cancer Inst.* 85:1644–1656 (1993)), associated metastases remain the major cause of breast cancer mortality (Frost, P. & Levin, R., *Lancet* 339:1458–1461 (1992)). The initial steps of transformation characterized by the malignant cell escape from normal cell cycle controls are driven by the expression of dominant oncogenes and/or the loss of tumor suppressor genes (Hunter, T. & Pines, J., *Cell* 79:573–582 (1994)).

Tumor progression can be considered as the ability of the malignant cells to leave the primary tumoral site and, after migration through lymphatic or blood vessels, to grow at a distance in host tissue and form a secondary tumor (Fidler, I. J., *Cancer Res.* 50:6130–6138 (1990); Liotta, L. et al., *Cell* 64:327–336 (1991)). Progression to metastasis is dependent not only upon transformation but also upon the outcome of a cascade of interactions between the malignant cells and the host cells/tissues. These interactions may reflect molecular modification of synthesis and/or of activity of different gene products both in malignant and host cells. Several genes involved in the control of tumoral progression have been identified and shown to be implicated in cell adhesion, extracellular matrix degradation, immune surveillance, growth factor synthesis and/or angiogenesis (reviewed in, Hart, I. R. & Saini, A., *Lancet* 339:1453–1461 (1992); Ponta, H. et al.,*B.B.A*. 1198:1–10(1994); Bernstein, L. R. & Liotta, L. A., *Curr. Opin. Oncol.* 6:106–113 (1994); Brattain, M. G. et al., *Curr. Opin. Oncol.* 6:77–81 (1994); and Fidler, I. J. & Ellis, L. M., *Cell* 79:185–188 (1994)).

However, defining the mechanisms involved in the formation and growth of metastases is still a major challenge in breast cancer research (Rusciano, D. & Burger, M. M., *BioEssays* 14:185–194 (1992); Hoskins, K. & Weber, B. L., *Current Opinion in Oncology* 6:554–559 (1994)). The processes leading to the formation of metastases are complex (Fidler, I. J., *Cancer Res.* 50:6130–6138 (1990); Liotta, L. et al., *Cell* 64:327–336 (1991)), and identifying the related molecular events is thus critical for the selection of optimal treatments.

SUMMARY OF THE INVENTION

In one aspect, the invention is directed to a method of treating a hyperproliferative disease in a subject, the method comprising: (a) administering to the subject a pharmaceutically effective amount of a retinoid X receptor (RXR) agonist; and (b) administering to the subject a pharmaceutically effective amount of an agent which is capable of activating protein kinase A (PKA). The method can further comprise (c) administering to the subject a pharmaceutically effective amount of a retinoic acid receptor (RAR) agonist. The method can further comprise (d) administering to the subject a pharmaceutically effective amount of a cytokine, with or without a pharmaceutically effective amount of an RAR agonist.

Also provided is a kit useful for carrying out the method of treating a hyperproliferative disease.

In another aspect, the invention is directed to a method of inhibiting proliferation of breast cancer cells by administering an RXR agonist and an agent capable of activating protein kinase A. Breast cancer cell lines include, but are not limited to, T47D.

In another aspect, the invention is directed to a pharmaceutical composition comprising (a') a retinoid X receptor (RXR) agonist and (b') an agent capable of activating protein kinase A (PKA). The composition can further comprise (c') a retinoic acid receptor (RAR) agonist. The composition can further comprise (d') a cytokine, with or without an RAR agonist (c').

RXR agonists include, but are not limited to, the group consisting of 9-cis retinoic acid, bexarotene, 4-[1-[5,6-Dihydro-3,5,5-trimethyl-8-(1-methylethyl)-2-naphthalenyl] ethenyl]benzoic acid, and SR11237.

The agent capable of activating PKA can be a PKA agonist. PKA agonists include, but are not limited to, 8-bromo-cAMP, Sp-cAMPS, 8CPT-cAMP, dibutyryl-cAMP, Sp-5,6-DCl-cBiMPS, adenylate cyclase toxin, forskolin, L-858051, and Sp-8-pCPT-cGMPS. Alternatively, the agent can be a compound that increases cAMP level, either by stimulating cAMP synthesis or by inhibiting a phosphodiesterase. Compounds which increase cAMP synthesis include, but are not limited to, adenylate cyclase toxin, forskolin, and L-85 8051. Compounds that act as inhibitors of phosphodiesterases include, but are not limited to, RO 20-1724, Rolipram, Etazolate, and 3-isobutyl-1-methylxanthine (IBMX).

RAR agonists include RARα, RARβ and RARγ agonists. Of course, an RAR agonist can be selective or specific for one or more of the RAR subtypes. RARα agonists include, but are not limited to, 9-cis retinoic acid, all-trans retinoic acid, 4-[[(2,3-Dihydro-1,1,3,3-tetramethyl-2-oxo-1H-inden-5-yl)carbonyl]amino] benzoic acid, AM-80, and AM-580.

Cytokines include, but are not limited to, a granulocyte colony-stimulating factor (G-CSF), granulocyte macrophage colony-stimulating factor (GM-CSF) and macrophage colony-stimulating factor (M-CSF).

In the method, steps (a)–(d) can be done concurrently, or in any order.

Hyperproliferative diseases can be, but are not limited to, cancer and psoriasis. Cancers include, but are not limited to, acute promyelocytic leukemia and breast cancer. The subject can be resistant to treatment with an RARα agonist alone.

BRIEF DESCRIPTION OF THE FIGURES

FIG. 1. Differential effects on NB4 cells of RAR and RXR specific agonists: evidence for positive cooperation between the retinoid and protein kinase A signaling pathways. Compounds were used as follows: ATRA, 1 μM; other retinoid receptor agonists, 0.2 μM; receptor antagonists, 2 μM; cell permeable cAMP analogue (8CPT-cAMP), 100 μM.

FIG. 2. Features of 4-[1-[5,6-Dihydro-3,5,5-trimethyl-8-(1-methylethyl)-2-naphthalenyl]ethenyl]benzoic acid (Compound V) as a bi-functional rexinoid.

carbonyl]amino]benzoic acid (Compound II), and 4-[1-[5,6-Dihydro-3,5,5-trimethyl-8-(1-methylethyl)-2-naphthalenyl]ethenyl]benzoic acid (Compound V) to elicit NBT response and CD11c expression in NB4 cells is shown in the right panels.

Figure 3A:
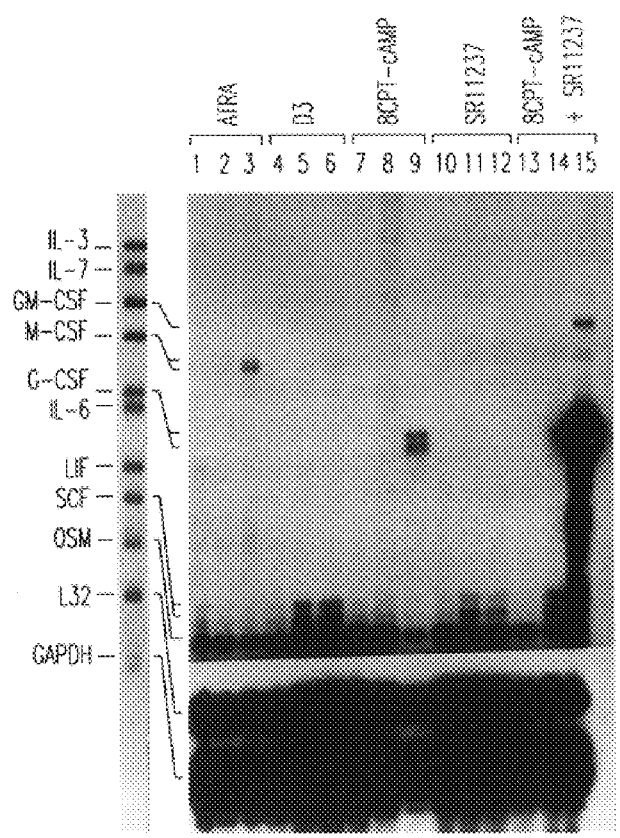
Figure 3B:
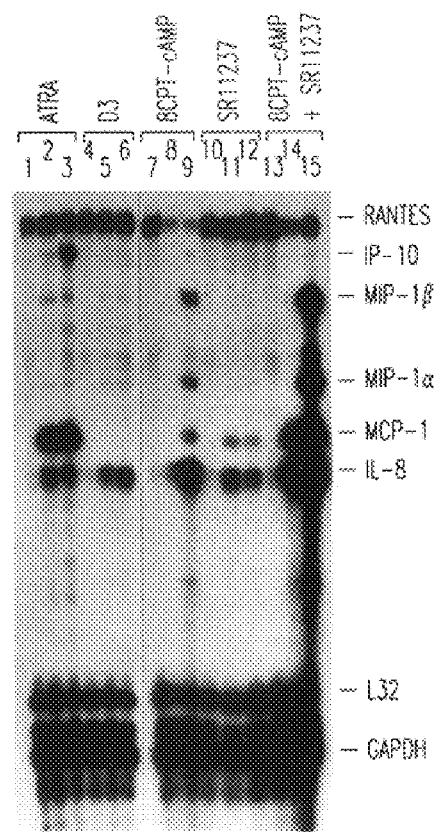

FIG. 3. Rexinoid-PKA crosstalk induces a cytokine expression program that differs from that induced by ATRA. Modulation of cytokine expression in NB4 cells was assessed by RNAse protection assays. Cells were exposed to the agents displayed at the top for 0, 24 and 48 h (subsequent lanes for each treatment). For comparison the effect of vitamin D3 ("D3") was studied also. FIG. 3a. The intact probes run on the same gel are shown on the left (L32 and GAPDH are the invariant internal controls used for calibration) and the positions of the protected fragments are indicated. FIG. 3b. Only the positions of the protected fragments are shown.

Figure 1A:
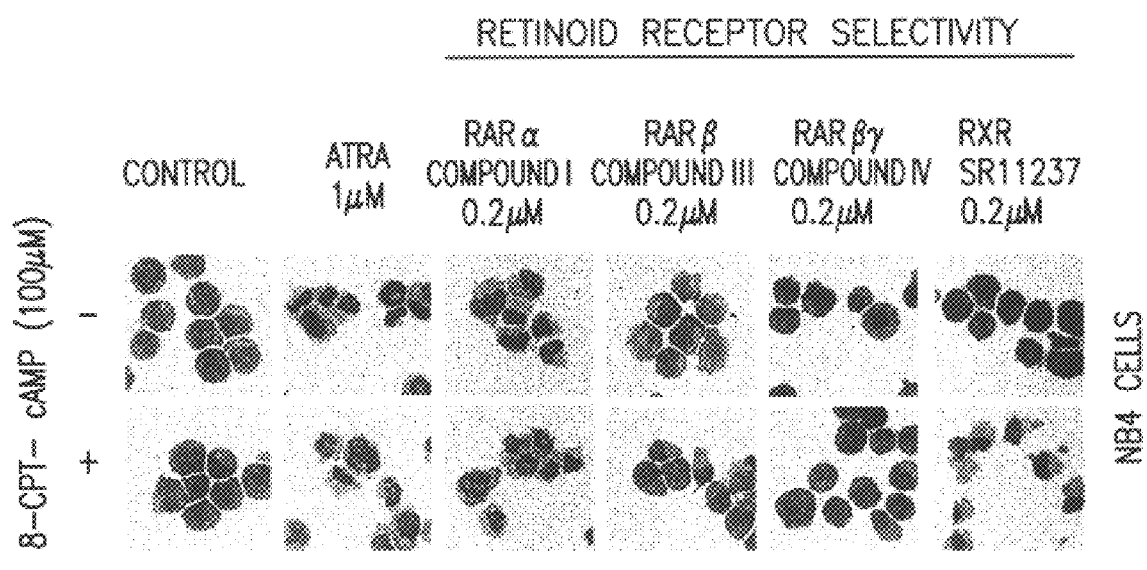
FIG. 1a. Morphological features of NB4 cells in response to treatments (after 72 h).
Figure 4A:
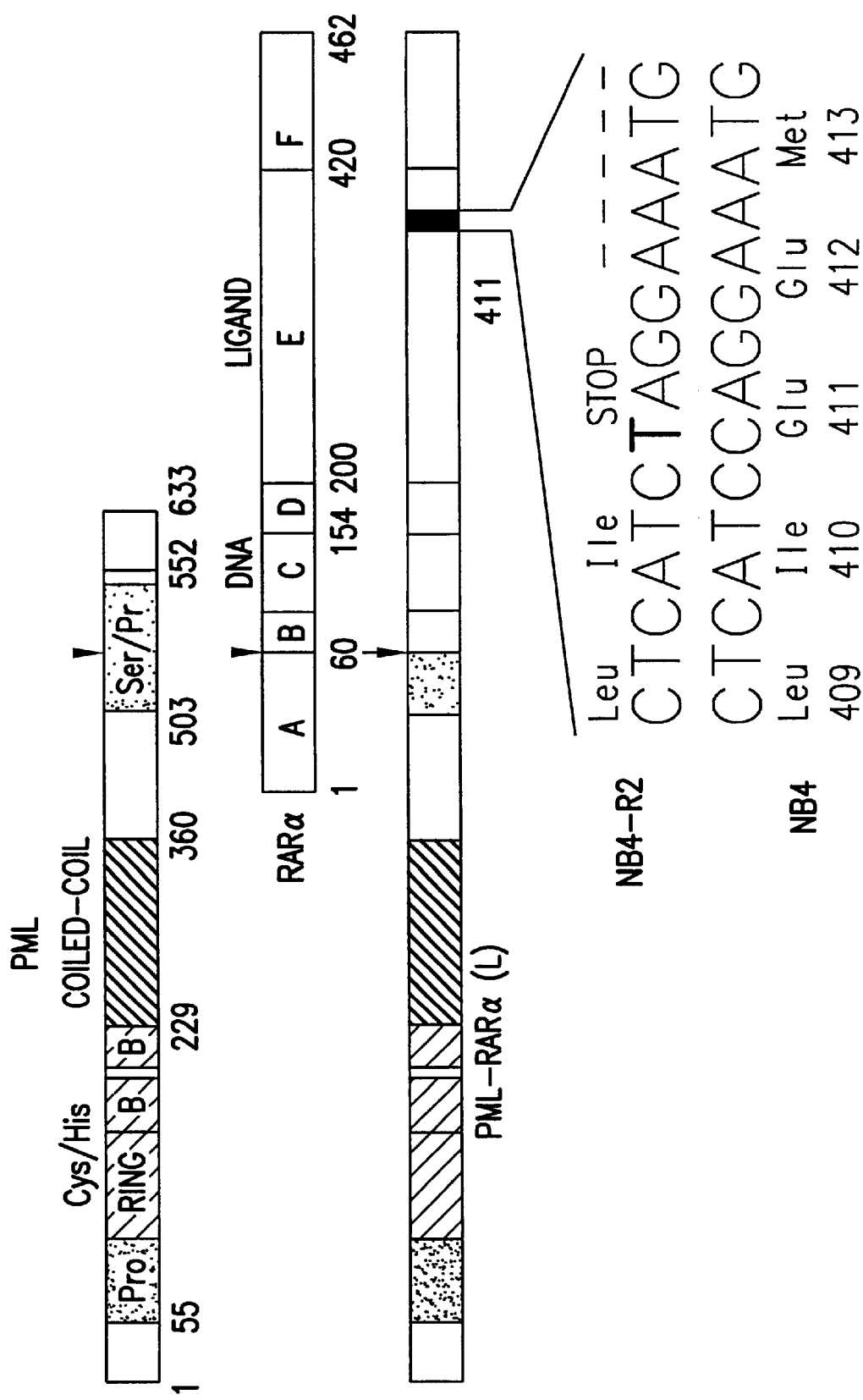
Figure 4B:
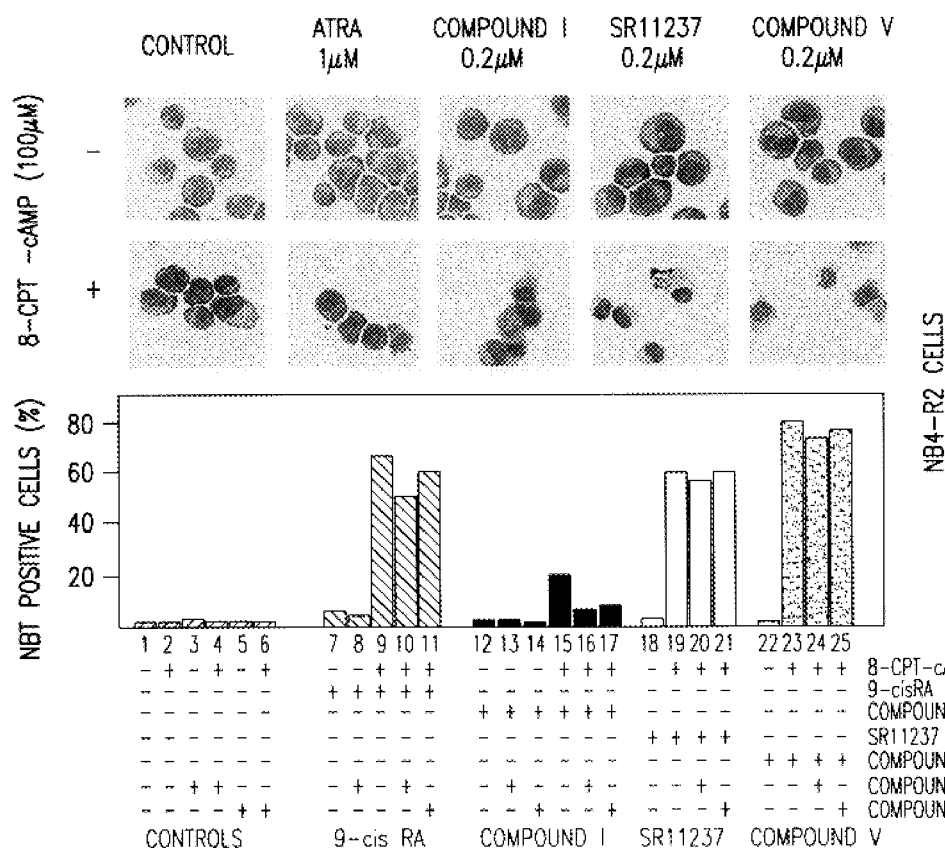

FIG. 4. A distinct RAR-ligand-independent signaling pathway triggers maturation of NB4-R2 cells resistant to RAR agonists. FIG. 4a. Molecular definition of the mutated PML-RARα in NB4-R2 cells. NB4-R2 is an ATRA-resistant subclone isolated from bone marrow leukemic cells of a ATRA-resistant patient by a selection with both cAMP and ATRA (Ruchaud, S. et al., Proc. Natl. Acad. Sci. U.S.A. 91:8428–8432 (1994); Duprez, E. et al., Leukemia 6:1281–1287 (1992)). The NB4-R2 cells carry the typical t(15;17) translocation and expressed PML-RAR/-60 mRNA, but not the 120 KD PML-RARα chimeric protein (Duprez, E. et al., Oncogene 12:2451–2459 (1996)). Sequencing oft he PML-RARα A cDNA reveals a point mutation generating a stop codon at the position 411 in the retinoid-binding domain of PML-RARα(L) (Kastner, P. et al., EMBO J. 11:629–642 (1992)) of NB4 cells, thus generating a truncated chimeric protein. FIG. 4b. Morphological and functional maturation of NB4-R2 cells in response to synergistic treatment by retinoids and 8-CPT-cAMP. NB4-R2 cells were treated with protocols similar to those used for NB4 cells (see description of FIG. 1). Note that cooperation between 8-CPT-cAMP and rexinoid signaling allows maturation of the ATRA-resistant cells.

Figure 5A:
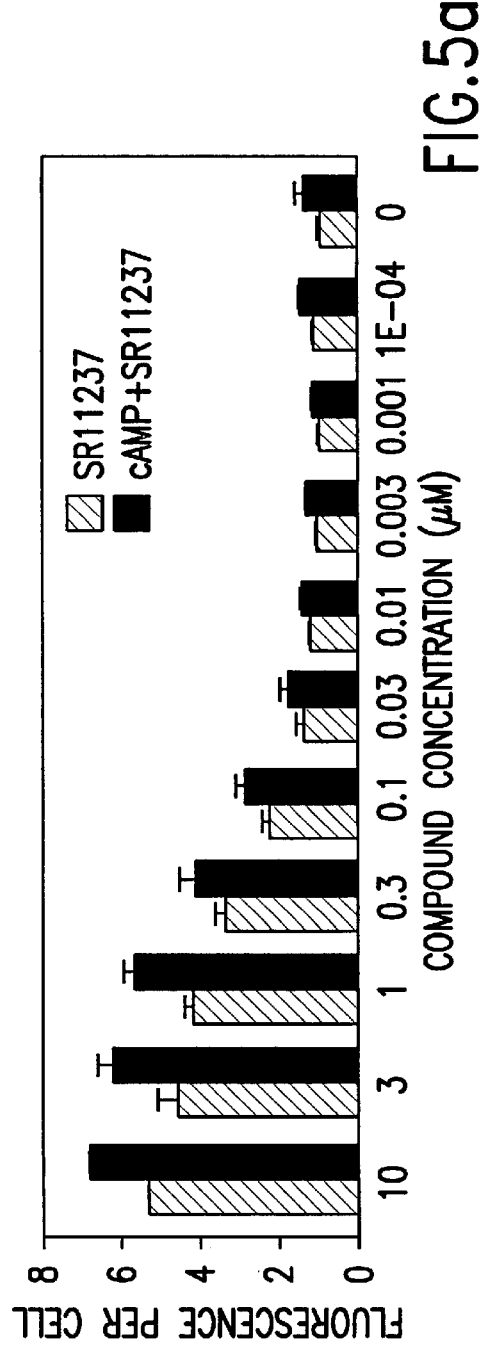
Figure 5B:
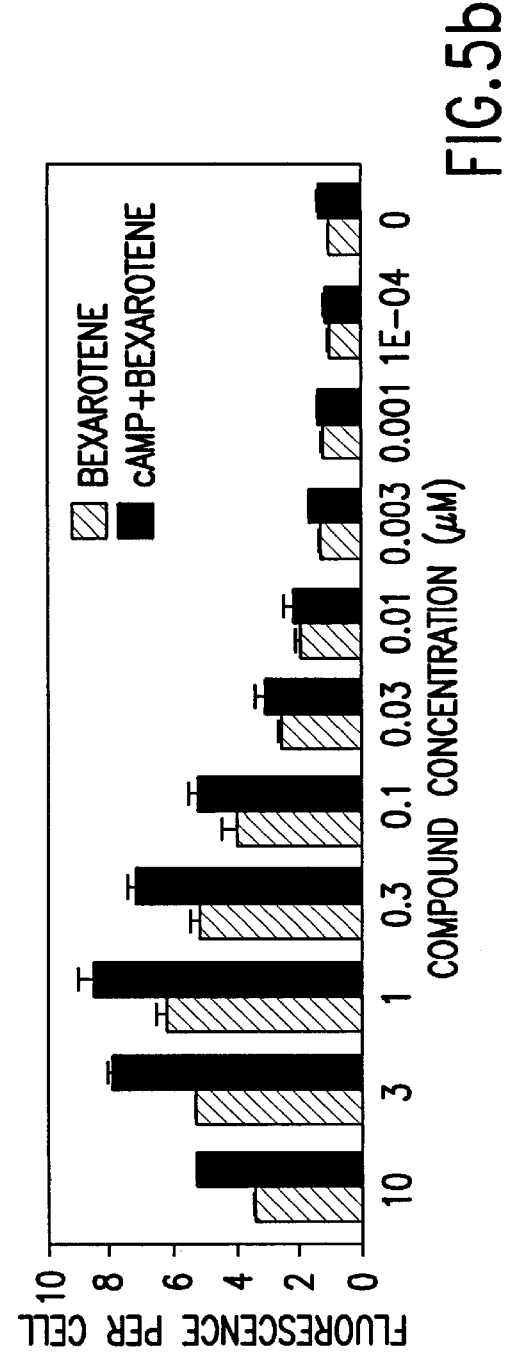

FIG. 5. Differentiation of T47D breast cancer cells. FIG. 5a. Effect of SR11237, with or without 8CPT-cAMP (100 μM), on lipid accumulation. FIG. 5b. Effect of bexarotene, with or without 8CPT-cAMP (100 μM), on lipid accumulation.

DETAILED DESCRIPTION OF THE PREFERRED EMBODIMENTS

It is provided herein an RARα-independent signaling pathway that induces maturation of both ATRA-sensitive (Lanotte, M. et al., Blood 77:1080–1086 (1991)) and ATRA-resistant (Ruchaud, S. et al., Proc. Natl. Acad. Sci. U.S.A. 91:8428–8432 (1994)) APL NB4 cells which is based on the crosstalk between RXR ligand ("rexinoid"; Mukherjee, R. et al., Nature 386:407–410 (1997)) and protein kinase A signaling. The results indicate the existence of a RXR-dependent promyelocyte maturation pathway that can be activated in the absence of the known ligands for RXR heterodimerization partners.

The invention provides an alternative therapy for hyperproliferative diseases, including APL, particularly in case of ATRA resistance, breast cancer and other hyperproliferative disorders dependent on protein kinase A activation.

This alterative therapy provides a treatment method with a higher therapeutic index (the ratio of efficacy to toxicity), as the known RXR agonists are generally less toxic than RAR agonists. Thus, the present invention provides a means to dramatically reduce the incidence of side-reactions.

The invention also provides a method of inhibiting proliferation of a breast cancer cell by administering an RXR agonist and an agent capable of activating protein kinase A.

RXR and RAR Agonists

A "retinoid" is a compound which binds to one or more of the retinoid receptors (RARα, RARβ, RARγ, RXRα, RXRβ and RXRγ). Compounds are either "RAR retinoids" or "RXR retinoids" depending on their binding characteristics (RAR retinoids bind to one or more RARs; RXR retinoids bind to one or more RXRs (also referred to as "rexinoids")). Retinoids which cause transactivation via their receptors are examples of "agonists," while retinoids which do not cause transactivation, but instead block the transactivation caused by other agonists, are examples of "antagonists." RXR and RAR agonists to be used in the methods of the present invention can be, but are not limited to, peptides, carbohydrates, steroids and vitamin derivatives, which may each be natural or synthetic (prepared, for example, using methods of synthetic organic and inorganic chemistry that are well-known in the art).

By retinoids that are "specific" for a retinoid receptor are intended compounds that only bind to a particular retinoid receptor. By retinoids that are "selective" for a retinoid receptor are intended compounds that preferably bind to a particular retinoid receptor over others by a magnitude of approximately five-fold or greater than to other retinoid receptors, preferably eight-fold or greater, more preferably, ten-fold or greater.

Standard retinoids known in the art as RAR agonists include the following:

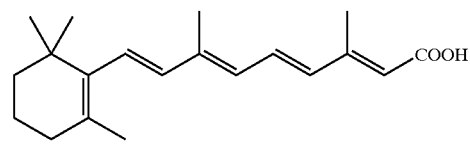

All-trans-retinoic acid

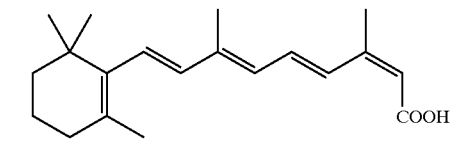

13-cis-retinoic acid

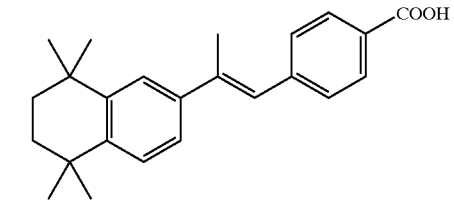

"Arotinoid"

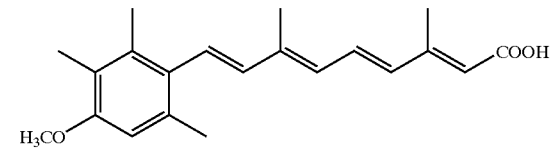

Acetretin

RARα,β-selective agonists include but are not limited to,

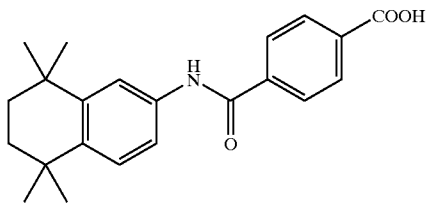

AM-80

(see, Takeuchi, M., et al., *Brit. J. Haematol.* 97:137–140 (1997)).

RARβ,γ-selective agonists include, but are not limited to,

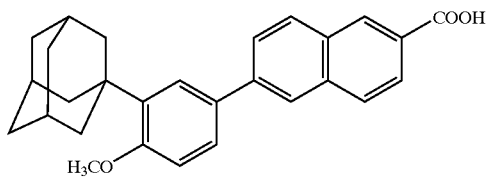

Adapalene (see, Shroot, B. and Michel, S., *J. Amer. Acad. Dermatol.* 36:S96–S103 (1997)).

RARγ agonists include, but are not limited to,

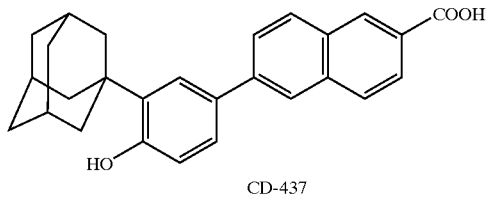

CD-437

(see, Schadendorf, D., et al., *Intl. J. Oncol.* 5:1325–1331 (1994)); and

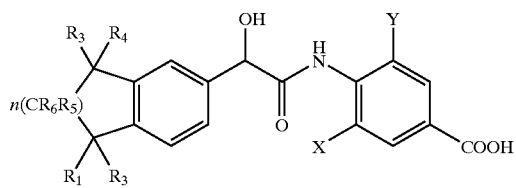

General structure

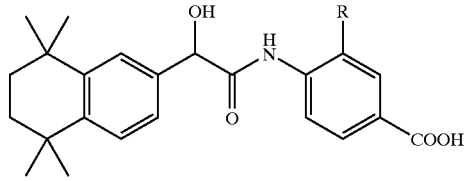

Specific example (see, Swann, R. T., et al., EP 747,347).

RAR agonists include, but are not limited to,

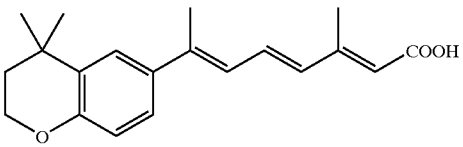

(see, Benbrook, D. M., et al., *J. Med. Chem.* 40:3567–3583 (1997));

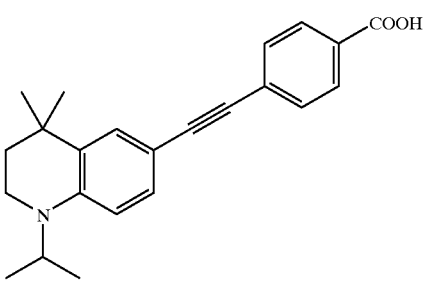

(see, Beard, R. L., et al., *Bioorg. Med. Chem. Lett.* 7:2372–2378 (1997)); and

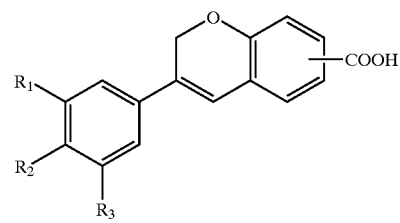

(see, Diaz, P., et al., *Bioorg. Med. Chem. Lett.* 7:2289–2294 (1997)).

Further, RARα specific or selective agonists can contain an amide group. RARγ specific or selective agonists can contain a hydroxyl group or a carbonyl group such as a flavone structure. RARβ specific or selective agonists can be characterized by the absence of a hydroxy and amide groups. Moreover, it has been determined that RARβ specific agonists can be characterized by a dihydronaphthalene nucleus bearing a 2-thienyl group at C8 (see, U.S. Pat. No. 5,559, 248; Johnson, A. T., et al., *J. Med. Chem.* 39:5029–5030 (1996)).

General RXR agonists include, but are not limited to, compounds of Formula I:

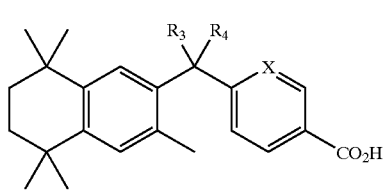

I wherein $R_3$, $R_4$ is —$CH_2CH_2$— or —$CH_2O$—, and X is CH or N, provided that if X is N, then $R_3$, $R_4$ is —$CH_2CH_2$—

(see, Boehm, M. F., et al., *J. Med. Chem.* 38:3146–3155 (1995)); compounds of Formula II:

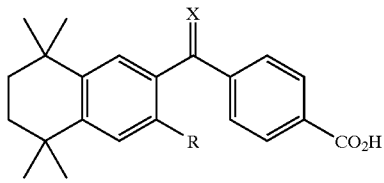

wherein R is hydrogen, methyl, ethyl, isopropyl, n-propyl, fluorine, chlorine, bromine, OH, or $OCH_3$, and X is O or $CH_2$ (see, Boehm et al., *J. Med Chem.* 37:2930–2941 (1994)); and compounds of Formula III:

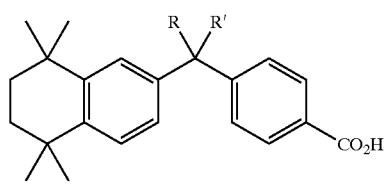

wherein R, R' is $—SCH_2CH_2CH_2S—$, $—(CH_3)_2C—$, $—SCH_2CH_2S—$, $—OCH_2CH_2S—$, $—OCH_2CH_2CH_2O—$, or $—OCH_2CH_2O—$ (see, Lehmann et al., *Science* 258:1944–1946 (1992); Pfahl et al., U.S. Pat. No. 5,552,271).

Specific RXR agonists include, but are not limited to,

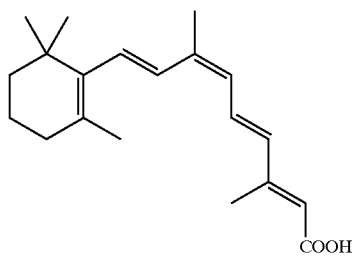

9-cis-Retinoic acid

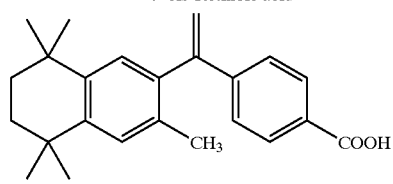

bexarotene

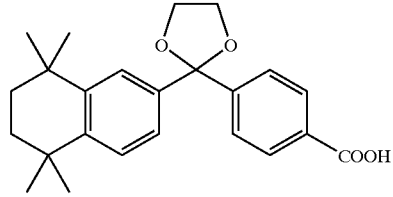

SRI-11237

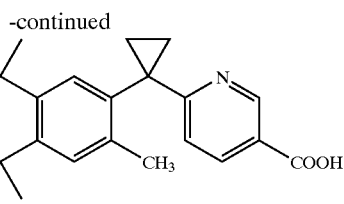

Additional RXR agonists include, but are not limited to,

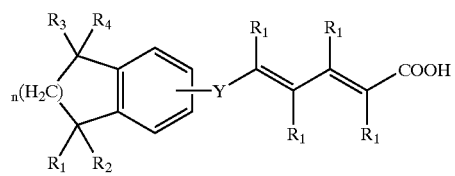

General structure

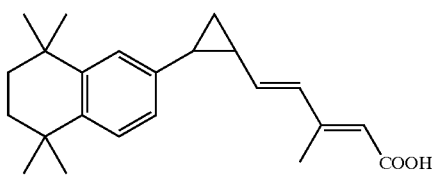

Specific example (see, Vuligonda, V. And R. A. Chandraratna, U.S. Pat. No. 5,675,033);

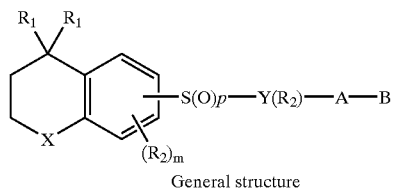

General structure

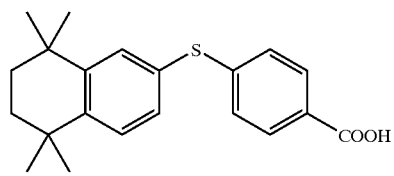

Specific example (see, Beard, R. L., et al., WO 97/16,422);

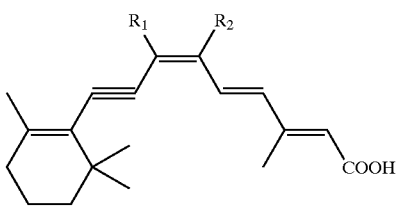

General structure

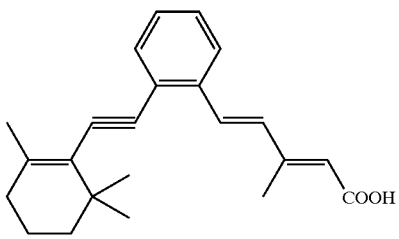

Specific example (see, Klaus, M., et al., EP 728,742);

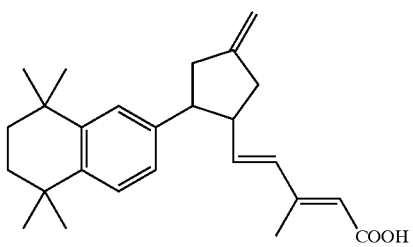

(see, Farmer, L. J., et al., *Bioorg. Med. Chem. Lett.* 7:2393–2398 (1997)); and

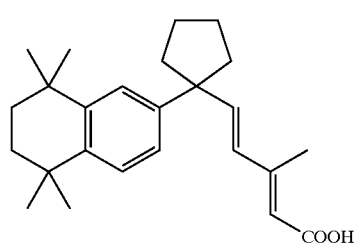

(see, Farmer, L. J., et al., *Bioorg. Med. Chem. Lett.* 7:2747–2752 (1997)).

RAR or RXR agonists include, but are not limited to,

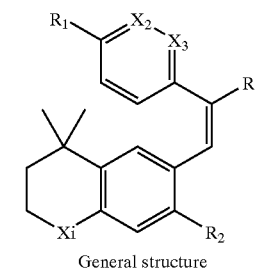

General structure

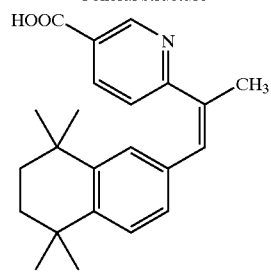

Specific example (Leblond, B., WO 97/26,237).

Other RXR agonists, with a variety of structures, are disclosed in Boehm, M. F., et al., *J. Med. Chem.* 38:3146–3155 (1995). Further, a number of retinoids of diverse structure types which are triple RAR agonists, selective RARα agonists, selective RARβ agonists, selective RARγ agonists, selective RARβ,γ agonists, selective RXR agonists and RXR/RAR pan-agonists are described in Sun, S. Y., et al., *Cancer Res.* 57:4931–4939 (1997). The invention can also be carried out with the RXR agonist bexarotene, the structure and preparation of which are described in Boehm et al., *J. Med. Chem.* 37:2930–2941 (1994). Other RXR agonists are also described in, for example, Lehmann et al., *Science* 258:1944–1946 (1992). Other candidate RAR and/or RXR agonists include, but are not limited to, 9-cis-Retinoic acid General structure Specific example (see, Bernardon, J. M., EP 722,928);

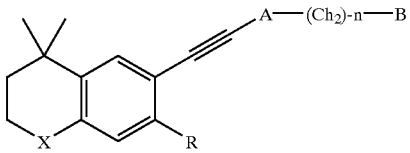

General structure

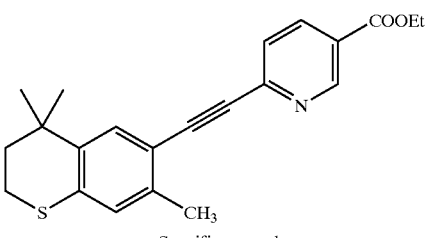

Specific example (see, Chandraratna, R., WO 96/11,686; and *Drugs of the Future* 22:249–255 (1997));

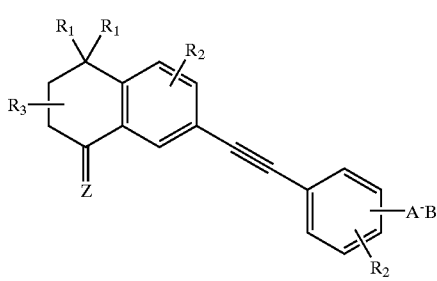

General structure

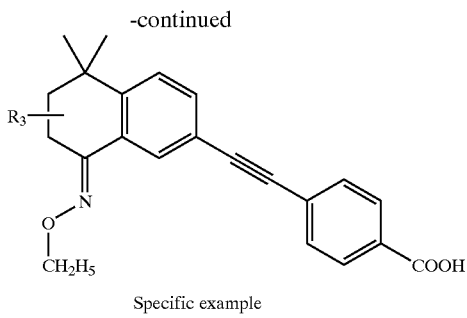

Specific example (see, Vuligonda, S., et al., U.S. Pat. No. 5,599,967);

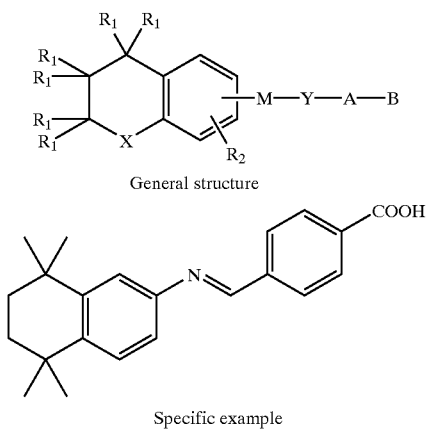

General structure

Specific example (see, Chandraratna, R. A. and M. Teng, WO 96/06,070);

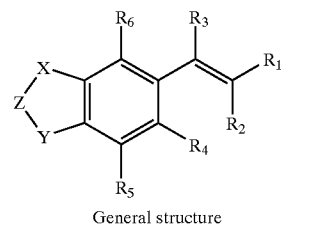

General structure

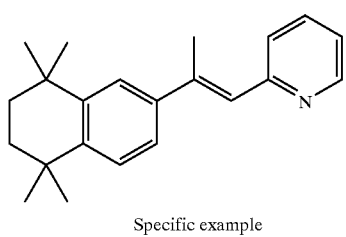

Specific example (see, Klaus, M. and E. Weis, EP 253,302);

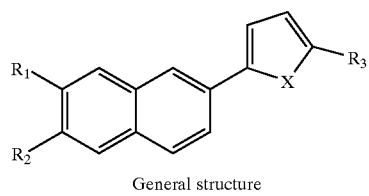

General structure

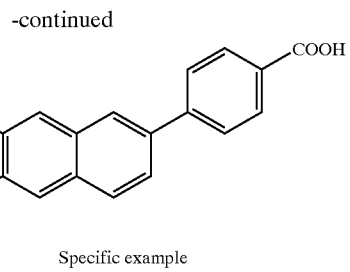

Specific example (see, Shroot, B. V., et al., EP 210,929); and

General structure

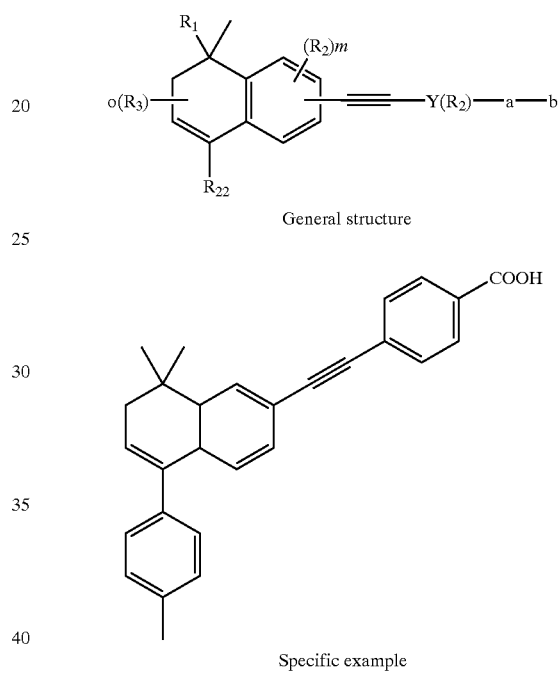

Specific example (see, Johnson, A. T., et al., U.S. Pat. No. 5,648,514).

Thus, preferred RXR agonists that can be used in the invention include, but are not limited to, 9-cis retinoic acid, 4-[1-[5,6-Dihydro-3,5,5-trimethyl-8-(1-methylethyl)-2-naphthalenyl]ethenyl]benzoic acid (Compound V; structure and synthesis provided in U.S. application Ser. No. 60/127,976, filed Apr. 6, 1999, titled "Selective Retinoic Acid Analogs"; and U.S. application Ser. No. 60/130,649, filed Apr. 22, 1999, titled "Selective Retinoic Acid Analogs", SR11237 (structure and synthesis provided in U.S. Pat. No. 5,552,271), and bexarotene. RARα agonists that can be used in the invention include, but are not limited to, all-trans retinoic acid, 4-[[(2,3-Dihydro-1,1,3,3-tetramethyl-2-oxo-1H-inden-5-yl)carbonyl]amino]benzoic acid (Compound I; structure and synthesis provided in WO 98/47861), AM-80 and AM-580.

For sake of brevity, the following designations will be used throughout this disclosure.

| Compound | Structure | CAS Name |
|---|---|---|
| I | 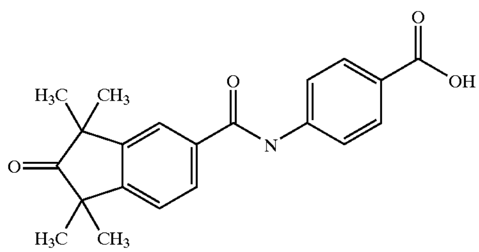 | 4-[[(2,3-Dihydro-1,1,3,3-tetramethyl-2-oxo-1H-inden-5-yl)carbonyl]amino]benzoic acid |
| II | 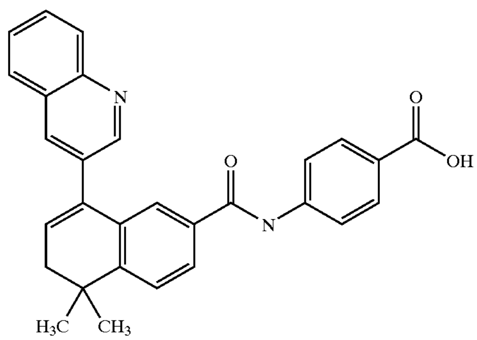 | 4-[[[5,6-Dihydro-5,5-dimethyl-8-(3-quinolinyl)-2-naphthalenyl]carbonyl]amino]benzoic acid |
| III | 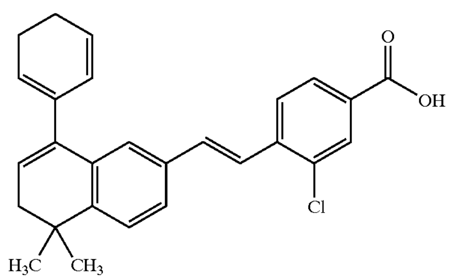 | (E)-3-Chloro-4-[2-(5,6-dihydro-5,5-dimethyl-8-phenyl-2-naphthalenyl)ethenyl]benzoic acid |
| IV | 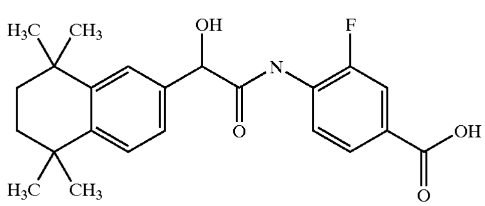 | 3-Fluoro-4[[(5,6,7,8-tetrahydro-5,5,8,8-tetramethyl-2-naphthalenyl)hydroxyacetyl]amino]benzoic acid |
| V | 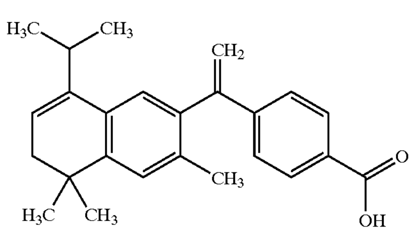 | 4-[1-[5,6-Dihydro-3,5,5-trimethyl-8-(1-methylethyl)-2-naphthalenyl]ethenyl]benzoic acid |

-continued

| Compound | Structure | CAS Name |
|---|---|---|
| VI | 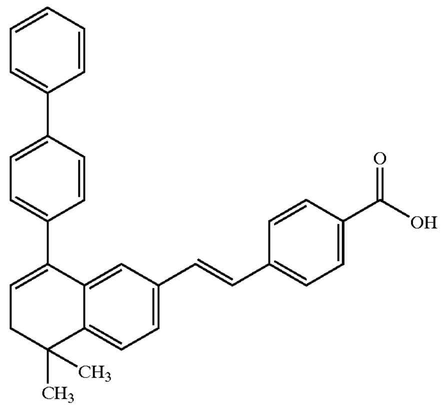 | (E)-4-2-[8-(1,1'-Biphenyl]-4-yl)-5,6-dihydro-5,5-dimethyl-2-naphthalenyl]ethenyl] benzoic acid |

Other RAR and RXR agonists suitable for use in the present invention may be prepared by the below-cited methods and others routine to those of ordinary skill in the art.

Screening Methods

A number of methods for screening candidate RXR and RAR agonists are well-known in the art, and will allow one of ordinary skill in the art to determine if a compound is useful in the present invention.

Such agonists can be selected and screened at random, or can be rationally selected or rationally designed using protein modeling techniques.

For random screening, agents such as, but not limited to, peptides, carbohydrates, steroids and vitamin derivatives (e.g., derivatives of retinoic acid) are selected at random and assayed using direct and indirect methods that are routine in the art, for their ability to bind to a retinoid receptor or a functional retinoid receptor heterodimer. Alternatively, agents can be assayed for RXR or RAR agonist activity.

Agents can be rationally selected. As used herein, an agent is said to be "rationally selected" when the agent is chosen based on the physical structure of a known ligand of a retinoid receptor or a functional homodimeric or heterodimeric retinoid receptor. For example, assaying compounds possessing a retinol-like structure would be considered a rational selection since retinol-like compounds are known to bind to a variety of retinoid receptor heterodimers.

Since highly purified RXR and RAR proteins are now available, X-ray crystallography and NMR-imaging techniques can be used to identify the structure of the ligand binding site present on these proteins and, by extension, that which is specifically present on the retinoid receptors. Utilizing such information, computer modeling systems are now available that allows one to "rationally design" an RXR or RAR agonist capable of binding to such a defined structure (Hodgson, *Biotechnology* 8:1245–1247 (1990); Hodgson, *Biotechnology* 9:609–613 (1991)).

As used herein, an agent is said to be "rationally designed" if it is selected based on a computer model of the ligand binding site of one or more retinoid receptor(s).

For example, in Chen, J.-Y. et al., *EMBO J.* 14:1187–1197 (1995), three "reporter" cell lines have been used to characterize a number of RARα-, RARβ-, or RARγ-specific dissociating synthetic retinoids that selectively induce the AF-2 activation function present in the LBD of RARβ (βAF-2). These cell lines stably express chimeric proteins containing the DNA binding domain of the yeast transactivator GAL4 fused to the EF regions (which contain the LBD and AF-2 activation function) of RARα (GAL-RARα), RARβ (GAL-RARβ) or RARγ (GAL-RARγ), and a luciferase reporter gene driven by a pentamer of the GAL4 recognition sequence ("17 m") in front of the β-globin promoter ((17 m)5-GAL-Luc). In these cell lines, the RAR ligands thus induce luciferase activity that can be measured in the intact cells using a single-photon-counting camera. This reporter system is insensitive to endogenous receptors which cannot recognize the GAL4 binding site. Using analogous screening assays, these synthetic retinoids, like RA, have been reported to inhibit the anchorage-independent growth of oncogene-transformed 3T3 cells, while the promoter of the human interleukin-6 (IL-6) gene, whose product is involved in the regulation of hematopoiesis, immune responses and inflammation (Kishimoto, T., et al., *Science* 258:593–597 (1992)) has been shown to be induced by RA but not by the synthetic dissociating retinoids which repressed its activity.

In a similar manner, RXR agonists have been identified using cell lines that express a RXR receptor linked to a TREpal-tk reporter gene which is activated by both RAR/RXR heterodimers and RXR homodimers (Lehmann, J. M., et al., *Science* 258:1944–1946 (1992)). Thus, reporter cell lines that are easily constructed, by methods routine to one of ordinary skill, can be used to distinguish not only the specific RXR or RAR types to which a candidate ligand will bind, but also whether that binding induces an activating (i.e., agonistic) or repressive (i.e., antagonistic) effect. Although the above-referenced reporter cell lines comprised the luciferase or thymidine kinase genes as reporters, other reporters such as Neo, CAT, β-galactosidase or Green Fluorescent Protein are well known in the art and can be used in a similar fashion to carry out the present invention. For example, references disclosing reporter plasmids containing a reporter gene and expression vectors encoding a LBD of a nuclear receptor include Meyer et al., *Cell* 57:433–442 (1989); Meyer et al., *EMBO J.* 9(12):3923–3932 (1990); Tasset et al., *Cell* 62:1177–1187 (1990); Gronemeyer, H., and Laudet, V., *Protein Profile* 2:1173–1308 (1995); Webster et al., *Cell* 54:199–207 (1988); Strahle et al., *EMBO J.* 7:3389–3395 (1988); Seipel et al., *EMBO J.* 11:4961–4968 (1992); and Nagpal, S., et al., *EMBO J.* 12:2349–2360 (1993).

Other routine assays have been used to screen compounds for their agonistic properties on functions of other nuclear receptors, such as steroid receptors. For example, a transient expression/gel retardation system has been used to study the effects of the synthetic steroids RU486 and R5020 on progesterone and glucocorticoid receptor functions, respectively (Meyer, M.-E., et al., *EMBO J*. 9:3923–3932 (1990)). Similar assays have been used to show that tamoxifen competitively inhibits estradiol-induced ERAP160 binding to the estrogen receptor, suggesting a mechanism for its growth-inhibitory effects in breast cancer (Halachimi, S., et al., *Science* 264:1455–1458 (1994)). Since the RXR and RAR receptors are apparently structurally similar to other nuclear receptors such as the steroid receptors (as reviewed in Chambon, P., *FASEB J*. 10:940–954 (1996)), routine assays of this type can be useful in assessing compounds for their agonistic activities on RAR and/or RXR receptors.

As an alternative routine method, the effect of a candidate agonist on the binding of the ligand-dependent AF-2 modulator TIF1 to a RXR or RARLBD can be studied using glutathione-S-transferase (GST) interaction assays by tagging the LBDs with GST as described in detail in Le Douarin et al., *EMBO J*. 14:2020–2033 (1995).

In another screening assay, transgenic animals, e.g., mice, and cell lines, that are altered in their expression of one or more of RAR and RXR receptors can be made as described previously (Krezel, W., et al., *Proc. Natl. Acad Sci. USA* 93:9010–9014 (1996)) and can be used to identify agonists of specific members of the RAR/RXR class of receptors using methods described previously (WO 94/26100). In such an assay, the agent which is to be tested will be incubated with one or more of the transgenic cell lines or mice or tissues derived therefrom. The level of binding of the agent is then determined, or the effect the agent has on biological effect or gene expression is monitored, by techniques that are routine to those of ordinary skill. As used herein, the term "incubate" is defined as contacting the compound or agent under investigation with the appropriate cell or tissue, or administering the agent or compound to the appropriate animal, e.g., transgenic mouse, via any one of the well-known routes of administration including enteral, intravenous, subcutaneous, and intramuscular.

Other assays can also be used to determine the agonistic effects of RXR and RAR ligands. For example, certain agonistic retinoids will induce the association of endogenous PML/PML-RARα fusion protein with nuclear bodies in cells from APL patients (Dyck, J. A., et al., *Cell* 76:333–343 (1994); Weis, K., et al., *Cell* 76:345–356 (1994); Koken, M. H. M., et al., *EMBO J*. 13:1073–1083 (1994)) or in related established cell lines such as NB4 (Lanotte, M., et al., *Blood* 77:1080–1086 (1991)). These effects of RXR or RAR agonists can be determined, for example, by various immunological techniques such as immunofluorescent or immunoelectron microscopy, using antibodies specific for PML, RAR and/or PML-RARα fusion proteins. RXR or RAR agonists can also be identified by their abilities to induce the in vitro differentiation (maturation) of certain established cell lines such as HL-60 myeloblastic leukemia cells (Nagy, L., et al., *Mol. Cell. Biol*. 15:3540–3551 (1995)), NB4 promyelocytic cells (Lanotte, M., et al., *Blood* 77:1080–1086 (1991), P19 or F9 embryonic carcinoma cells (Roy, B., et al., *Mol. Cell. Biol*. 15:6481–6487 (1995); Horn, V., et al., *FASEB J*. 10:1071–1077 (1996)), or ras-transformed 3T3 cells (Chen et al., *EMBO J*. 14:1187–1197 (1995)). Ligand-induced differentiation in these and other cell lines can be determined by assaying ligand-treated or -untreated cells for the expression of a variety of well-known markers of differentiation as generally described in the above references.

Similarly, the candidate antagonists or agonists can be screened by measuring their abilities to induce apoptosis (programmed cell death) in, for example, HL-60 cells (Nagy, L., et al., *Mol. Cell. Biol*. 15:3540–3551 (1995)) or P19 cells (Horn, V., et al., *FASEB J*. 10:1071–1077 (1996)), or in other primary cells or established cell lines. Apoptosis is typically assessed by measurement of ligand-induced DNA fragmentation, which is accomplished by methods such as gel electrophoresis (appearance of smaller molecular weight bands), microscopy (changes in plasma membrane morphology such as formation of surface protuberances ("blebbing") or in nuclear morphology such as pycnosis or fragmentation) or expression of the putative apoptosis suppressive protein BCL-2 (decreased in apoptotic cells); for general methods and discussions of these assays as they pertain to RXR and RAR biology, see Nagy, L., et al., *Mol. Cell. Biol*. 15:3540–3551 (1995); Horn, V., el al., *FASEB J*. 10:1071–1077 (1996)). Other methods for assaying ligand-induced apoptosis in primary cells and established cell lines, such as flow cytometry or particle analysis (appearance of smaller particles with different light scatter and/or DNA content profiles) are well-known in the art (Telford, W. G., et al., *J. Immunol. Meth*. 172:1–16 (1994); Campana, D., et al., *Cytometry* 18:68–74 (1994); Sgonc, R. and Wick, G., *Int. Arch. Allergy Immunol*. 105:327–332 (1994); Fraker, P. J., et al., *Meth. Cell Biol*. 46:57–76 (1995); Sherwood, S. W., and Schimke, R. T., *Meth. Cell Biol*. 46:77–97 (1995); Carbonari, M., et al., *Cytometry* 22:161–167 (1995); Mastrangelo, A. J. and Betenbaugh, M. J., *Curr Opin. Biotechnol*. 6:198–202 (1995)).

Screening of agonists can be accomplished by an assay known as "in vivo footprinting" (Mueller, P. R., and Wold, B., *Science* 246:780–786 (1989); Garrity, P. A., and Wold, B. J., *Proc. Natl. Acad. Sci. USA* 89:1021–1025 (1992)), which has proven useful for analysis of RA-induced transcription of RARβ2 (Dey, A., et al., *Mol. Cell. Biol*. 14:8191–8201 (1994)).

Other methods for determining the agonistic activities of a candidate ligand which are routine in the art can also be used in carrying out the present invention. In performing such assays, one skilled in the art will be able to determine which RXR, or RAR receptor subtype(s), an agent binds to, what specific receptor(s) are utilized by a given compound, and whether the agent is an agonist of the given receptor(s).

Agents that Activate Protein Kinase A

Cyclic adenosine monophosphate (cAMP) is an intracellular mediator of hormone action in prokaryotic and animal cells. Such hormone-induced cellular responses include thyroid hormone secretion, cortisol secretion, progesterone secretion, glycogen breakdown, bone resorption, and regulation of heart rate and force of heart muscle contraction. Cyclic AMP-dependent protein kinase A (PKA) is found in all animal cells and is thought to account for all the effects of cAMP in most of these cells. In its inactive state, PKA consists of a complex of two catalytic subunits and two regulatory subunits. When each regulatory subunit of PKA has bound two molecules of cAMP, the catalytic subunit is activated and can transfer a high energy phosphate from ATP to the serine or threonine of a substrate protein. Altered PKA expression is implicated in a variety of disorders and diseases including thyroid disorders, diabetes, atherosclerosis, and cardiovascular disease.

It has been determined that administration of a PKA agonist in conjunction with an RXR agonist causes differentiation of NB4 cells (APL cell line) and breast cancer cells. PKA agonists known in the art include, but are not limited to, 8-bromo-cAMP (8-Bromoadenosine-3',5'-cyclic monophosphate, sodium salt), Sp-cAMPS (Sp-Adenosine-3',5'-cyclic monophosphorothioate), 8CPT-cAMP (8-(4-Chlorophenylthio)-adenosine-3',5'-cyclic monophosphate, sodium salt), dibutyryl-cAMP ($N^6,2'$—O-Dibutyryladenosine-3',5'-cyclic monophosphate, sodium salt monohydrate), Sp-5,6-DCl-cBiMPS (Sp-5,6-dichloro-1-β-D-ribofuranosylbenzimidazole-3',5'-monophosphorothioate), adenylate cyclase toxin (AC toxin), forskolin, L-858051 (7-Deacetyl-7β-(γ-N-methylpiperazino)-butyrylforskolin.2HCl), and Sp-8-pCPT-cGMPS. Such PKA agonists are available, for example, from BIOMOL, Pa., USA.

Thus, in another embodiment of the invention, the agent which activates PKA can be a compound that increases cAMP level. Cyclic AMP level can be increased by cAMP synthesis. Compounds that increase cAMP synthesis include, but are not limited to, adenylate cyclase toxin, forskolin, and L-858051. Phosphodiesterases (PDEs) degrade intracellular cAMP. Thus, an agent which activates PKA can be a compound which blocks degradation and thus inhibits cyclic nucleotide PDE activity. Compounds that inhibit PDE include, but are not limited to, RO 20-1724 (4-(3-Butoxy-4-methyoxybenzyl)-2-imidazolidinone), Rolipram, Etazolate, and IBMX (3-isobutyl-1-methylxanthine). Such PDE inhibitors are available, for example, from BIOMOL, Pa., USA.

Other agents capable of activating PKA that are suitable for use in the present invention can be prepared or known by those of ordinary skill in the art.

In the invention, an agent capable of activating PKA is administered in a pharmaceutically effective amount for treatment of hyperproliferative diseases.

A biological assay for elevation of intracellular cAMP is the transcriptional activation of reporter genes containing a cAMP-responsive element (CRE). The sequence of events is: (1) increased cAMP level, (2) activation of PKA and nuclear translocation of its catalytic subunit, (3) phosphorylation by the catalytic subunit, and thereby activation, of nuclear CRE binding protein (CREB), (4) activation of transcription upon binding of CREB to the CRE element. Using engineered reporter cells any agent that increases intracellular cAMP level could be identified by this method (Brindle, P. K. & Montminy, M. R., *Curr. Op. Genet. Devel.* 2:199–204 (1992); Lee, K. A. & Masson, N., *Biochim. Biophys. Acta* 1174:221–233 (1993)).

Biological assays for identifying other PDE inhibitors can be found in Conti, M. et al., *Endocrine Reviews* 16:370–389 (1995).

Cylokines

Cytokines are biological response modifiers that coordinate antibody and T cell immune system interactions and amplify immune reactivity (see, Abbas, A.K., et al., *Cellular and Molecular Immunology*, 2nd ed., 1994). Cytokines include, but are not limited to, monokines synthesized by macrophage and lymphokines produced by activated T lymphocytes and natural killer cells and other growth factors. Monokines include, but are not limited to, interleukin-1, tumor necrosis factor, α and β interferon, and colony-stimulating factors. Lymphokines include, but are not limited to, interleukins (e.g., IL-1 and IL-2), gamma interferon, granulocyte-macrophage colony-stimulating factor, and lymphotoxin. Other general growth factors include, but are not limited to, EGF, TGFβ and bFGF.

Chemokines are a family of structurally homologous 8 to 10 KD chemotactic cytokines. Chemokines are chemokinetic and chemotactic, stimulating leukocyte movement and directed movement.

Granulocyte-macrophage colony-stimulating factor (GM-CSF), granulocyte colony-stimulating factor (G-CSF) and macrophage colony-stimulating factor (M-CSF) are hematopoietic growth factors that stimulate proliferation and differentiation of normal myeloid and monocyte-macrophage precursors. GM-CSF enhances the function of differentiated cells such as mature peripheral blood neutrophils and mononuclear phagocytes. Its action is mediated by binding to GM-CSF-specific membrane receptors.

Administration of G-CSF, which was shown to enhance differentiation of APL cells induced by ATRA in vitro, combined with ATRA can improve the hematological state in APL patients not previously receiving ATRA therapy (Usuki, K. et al., *Intl. J. Hematol.* 64:213–219 (1996)). G-CSF was shown to be useful for augmenting susceptibility of APL cells to cell-cycle specific agents (Katayama, N. et al., *Am. J. Hematol.* 58:31–35 (1998)).

In the invention, cytokines including, but not limited to, G-CSF, GM-CSF and M-CSF can additionally be administered in a pharmaceutically effective amount for treatment of cancers and other hyperproliferative diseases.

Hyperproliferative Diseases

By "hyperproliferative disease" is intended, a disease resulting from rapid cell division. Hyperproliferative diseases include, but are not limited to, cancer, psoriasis, actinic keratosis and lamellar ichthyosis. Cancer cells are invasive and move to adjacent tissues whereas psoriasis and lamellar ichthyosis are noninvasive.

Cancer can be oral, skin, head and neck cancers. The cancer can be breast cancer. The cancer can be squamous cell carcinoma of the cervix and the skin, and Kaposi's sarcoma. Skin cancers include, but are not limited to, chronic sunlight damage, nevoid basal cell carcinoma syndrome, xeroderma pigmentosum, multiple keratoacanthomas, and cutaneous metastasis of malignant melanoma. Preferably, the cancer is acute promyelocytic leukemia or breast cancer.

Psoriasis include, but are not limited to, psoriasis vulgaris, pustular psoriasis, erythrodermic psoriasis and psoriatic arthritis.

For other retinoid related diseases, generally, see *The Retinoids: Biology, Chemistry, and Medicine*, Sporn, M. B. et al., eds., Raven Press, Ltd., New York, N.Y. (1994).

The term "subject" or "patient" as used herein is intended an animal, preferably a mammal, including a human. By "patient" is intended a subject in need of treatment of a hyperproliferative disease.

Formulation and Methods of Administration

As used herein, "a pharmaceutically effective amount" is intended an amount effective to elicit a cellular response that is clinically significant, without excessive levels of side effects.

A pharmaceutical composition oft he invention is thus provided comprising one or more RXR agonists and one or more agents capable of activating PKA (such as those described above), and a pharmaceutically acceptable carrier or excipient. The pharmaceutical composition can further comprise one or more RAR agonists (RARα, RARβ and/or RARγ), and can further comprise one or more cytokines.

The pharmaceutical composition can be administered orally, rectally, parenterally, intrasystemically, intravaginally, intraperitoneally, topically (as by powders, ointments, drops or transdermal patch), bucally, or as an oral or nasal spray. By "pharmaceutically acceptable carrier" is intended, but not limited to, a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

A pharmaceutical composition of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as olive oil), and injectable organic esters such as ethyl oleate. Proper fluidity can be maintained, for example, by the use of coating materials such as lecithin, by the maintenance of the required particle size in the case of dispersions, and by the use of surfactants.

The compositions of the present invention can also contain adjuvants such as, but not limited to, preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid, and the like. It can also be desirable to include isotonic agents such as sugars, sodium chloride, and the like. Prolonged absorption of the injectable pharmaceutical form can be brought about by the inclusion of agents which delay absorption such as aluminum monostearate and gelatin.

In some cases, in order to prolong the effect of the drugs, it is desirable to slow the absorption from subcutaneous or intramuscular injection. This can be accomplished by the use of a liquid suspension of crystalline or amorphous material with poor water solubility. The rate of absorption of the drug then depends upon its rate of dissolution which, in turn, can depend upon crystal size and crystalline form. Alternatively, delayed absorption of a parenterally administered drug form is accomplished by dissolving or suspending the drug in an oil vehicle.

Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter, or by incorporating sterilizing agents in the form of sterile solid compositions which can be dissolved or dispersed in sterile water or other sterile injectable medium just prior to use.

Solid dosage forms for oral administration include, but are not limited to, capsules, tablets, pills, powders, and granules. In such solid dosage forms, the active compounds are mixed with at least one item pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hardfilled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include, but are not limited to, pharmaceutically acceptable emulsions, solutions, suspensions, syrups and elixirs. In addition to the active compounds, the liquid dosage forms can contain inert diluents commonly used in the art such as for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, can contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

Topical administration includes administration to the skin or mucosa, including surfaces of the lung and eye. Compositions for topical administration, including those for inhalation, can be prepared as a dry powder which can be pressurized or non-pressurized. In nonpressurized powder compositions, the active ingredients in finely divided form can be used in admixture with a larger-sized pharmaceutically acceptable inert carrier comprising particles having a size, for example, of up to 100 $\mu$m in diameter. Suitable inert carriers include sugars such as lactose. Desirably, at least 95% by weight of the particles of the active ingredient have an effective particle size in the range of 0.01 to 10 $\mu$m.

Alternatively, the composition can be pressurized and contain a compressed gas, such as nitrogen or a liquefied gas propellant. The liquefied propellant medium and indeed the total composition is preferably such that the active ingredients do not dissolve therein to any substantial extent. The pressurized composition can also contain a surface active agent. The surface active agent can be a liquid or solid non-ionic surface active agent or can be a solid anionic surface active agent. It is preferred to use the solid anionic surface active agent in the form of a sodium salt.

A further form of topical administration is to the eye. The compounds of the present invention can be delivered in a pharmaceutically acceptable ophthalmic vehicle, such that the compounds are maintained in contact with the ocular surface for a sufficient time period to allow the compounds to penetrate the corneal and internal regions of the eye, for example, the anterior chamber, posterior chamber, vitreous body, aqueous humor, vitreous humor, cornea, iris/ciliary, lens, choroid/retina and sclera. The pharmaceutically acceptable ophthalmic vehicle can be, for example, an ointment, vegetable oil or an encapsulating material.

Compositions for rectal or vaginal administration are preferably suppositories which can be prepared by mixing the compounds of the invention with suitable non-irritating excipients or carriers such as cocoa butter, polyethylene glycol or a suppository wax which are solid at room temperature but liquid at body temperature and therefore melt in the rectum or vaginal cavity and release the drugs.

The compositions of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to the compounds of the invention, stabilizers, preservatives, excipients, and the like. The preferred lipids are the phospholipids and the phosphatidyl cholines (lecithins), both natural and synthetic. Methods to form liposomes are known in the art (see, for example, Prescott, Ed., *Meth. Cell Biol.* 14:33 et seq (1976)).

Kits

A kit is useful for carrying out the present invention. The kit can have a carrier means being compartmentalized in close confinement to receive two or more container means therein, having (1) a first container means containing a therapeutically effective amount of a RXR agonist and (2) a second container means containing a therapeutically effective amount of an agent which activates PKA. Optionally, the kit can have additional container mean(s) containing a therapeutically effective amount of a RAR agonist and/or cytokine.

Dosaging

One of ordinary skill will appreciate that effective amounts of the various agents of the invention, RXR agonists, agents capable of activating PKA, RAR agonists, and cytokines, can be determined empirically and can be employed in pure form or, where such forms exist, in pharmaceutically acceptable salt, ester or prodrug form. The agents can be administered to a patient in need thereof as pharmaceutical compositions in combination with one or more pharmaceutically acceptable excipients. It will be understood that, when administered to a human patient, the total daily usage of the agents or composition of the present invention will be decided by the attending physician within the scope of sound medical judgement. The specific therapeutically effective dose level for any particular patient will depend upon a variety of factors: the type and degree of the cellular response to be achieved; activity of the specific agent or composition employed; the specific agents or composition employed; the age, body weight, general health, sex and diet of the patient; the time of administration, route of administration, and rate of excretion of the agent; the duration of the treatment; drugs used in combination or coincidental with the specific agent; and like factors well known in the medical arts. For example, it is well within the skill of the art to start doses of the agents at levels lower than those required to achieve the desired therapeutic effect and to gradually increase the dosages until the desired effect is achieved.

For example, satisfactory results are obtained by oral administration of the compounds at dosages on the order of from 0.05 to 10 mg/kg/day, preferably 0.1 to 7.5 mg/kg/day, more preferably 0.1 to 2 mg/kg/day, administered once or, in divided doses, 2 to 4 times per day. On administration parenterally, for example by i.v. drip or infusion, dosages on the order of from 0.01 to 5 mg/kg/day, preferably 0.05 to 1.0 mg/kg/day and more preferably 0.1 to 1.0 mg/kg/day can be used. Suitable daily dosages for patients are thus on the order of from 2.5 to 500 mg p.o., preferably 5 to 250 mg p.o., more preferably 5 to 100 mg p.o., or on the order of from 0.5 to 250 mg i.v., preferably 2.5 to 125 mg i.v. and more preferably 2.5 to 50 mg i.v.

Dosaging can also be arranged in a patient specific manner to provide a predetermined concentration of the agents in the blood, as determined by techniques accepted and routine in the art (HPLC is preferred). Thus patient dosaging can be adjusted to achieve regular on-going blood levels, as measured by HPLC, on the order of from 50 to 1000 ng/ml, preferably 150 to 500 ng/ml.

It will be readily apparent to one of ordinary skill in the relevant arts that other suitable modifications and adaptations to the methods and applications described herein can be made without departing from the scope of the invention or any embodiment thereof.

As described herein, by "compound" is intended a protein, nucleic acid, carbohydrate, lipid or a small molecule.

The following Examples serve only to illustrate the invention, and are not to be construed as in any way to limit the invention.

EXAMPLES

Example 1

Figure 1B:
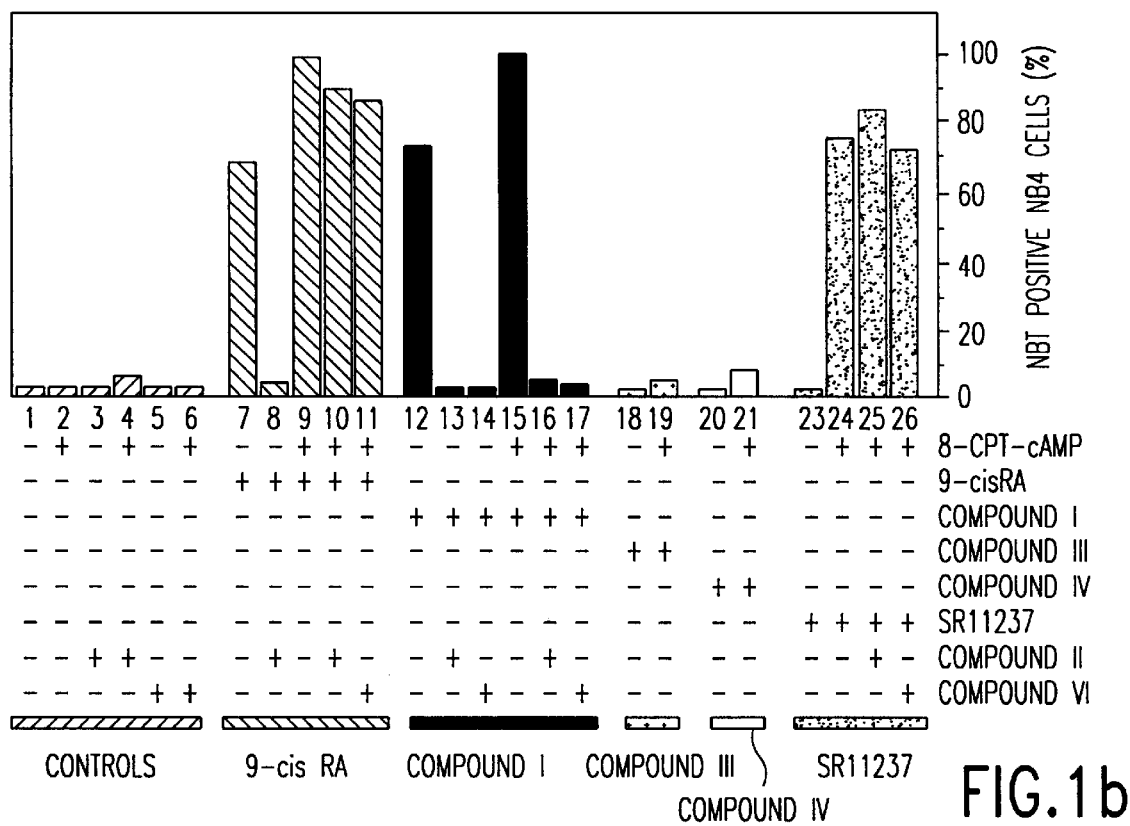
FIG. 1b. Nitroblue tetrazolium enzymatic reduction in retinoid-treated NB4 cells (after 72 h; percent of positive cells).
Figure 1C:
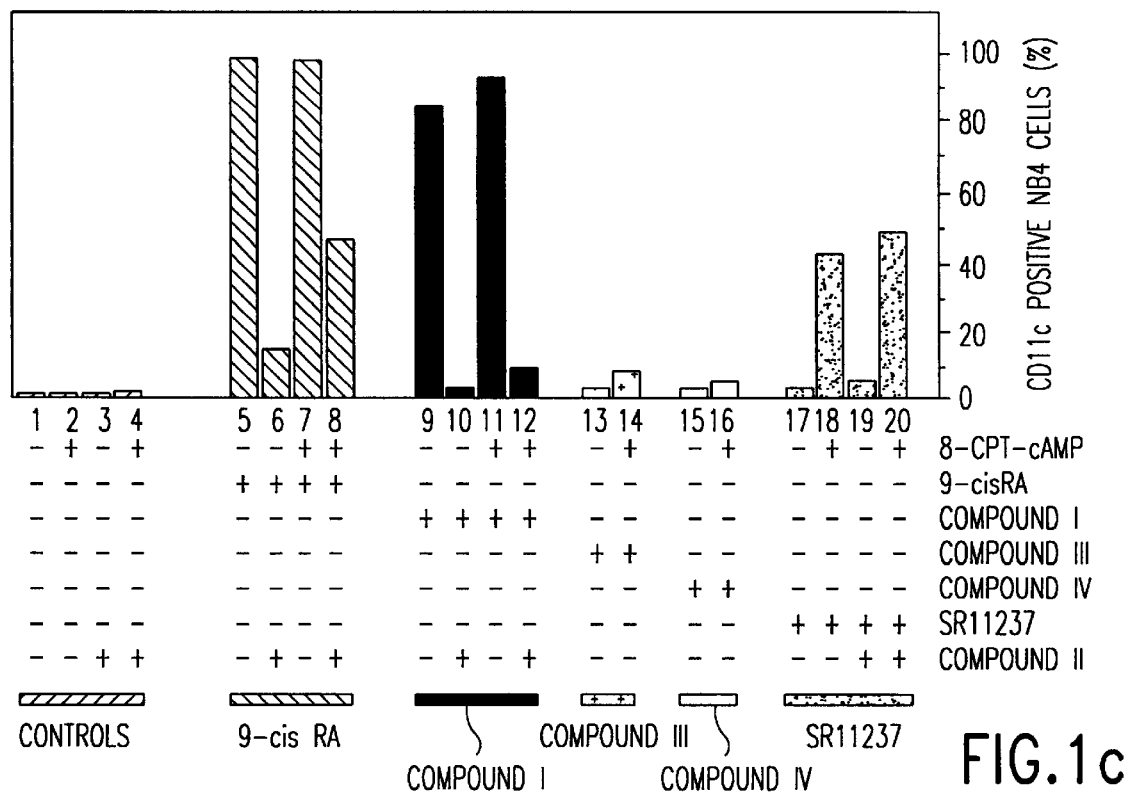
FIG. 1c. Flow-cytometry analysis of CD11c integrin expression following treatment of NB4 cells by retinoids and 8CPT-cAMP (after 48 h). Pan-agonists (ATRA, 9-cis RA) and RARα agonists (4-[[(2,3-Dihydro-1,1,3,3-tetramethyl-2-oxo-1H-inden-5-yl) carbonyl]amino]benzoic acid (Compound I)) but not RARβ ((E)-3-Chloro-4-[2-(5,6-dihydro-5,5-dimethyl-8-phenyl-2-naphthalenyl)ethenyl]benzoic acid (Compound III)) and RARβγ (3-Fluoro-4[[(5,6,7,8-tetrahydro-5,5,8,8-tetramethyl-2-naphthalenyl)hydroxyacetyl]amino]benzoic acid (Compound IV)) agonists induce NB4 cell maturation. On its own the RXR pan-agonist SR11237 failed to trigger NB4 cell maturation. However, consistent with an RXR-ligand dependent signaling, co-treatment with SR11237 and 8CPT-cAMP induces maturation of NB4 cells through a pathway that is not inhibited by the RAR antagonists 4-[[[5, 6-Dihydro-5,5-dimethyl-8-(3-quinolinyl)-2-naphthalenyl] carbonyl]amino]benzoic acid (Compound II) or (E)4-[2-[8-(1,1'-Biphenyl]-4-yl)-5,6-dihydro-5,5-dimethyl-2-naphthalenyl]ethenyl]benzoic acid (Compound VI).

As reported previously (Chen, J. Y. et al., *Nature* 382:819–822 (1996)), all RARα agonists (ATRA, 9-cis RA, 4-[[(2,3-Dihydro-1,1,3,3-tetramethyl-2-oxo-1H-inden-5-yl) carbonyl]amino]benzoic acid (Compound I)); the activities of all ligands discussed are summarized in Table 1) induce maturation of NB4 cells (FIG. 1a, top panel; FIG. 1b, lanes 7, 12; FIG. 1c, lanes 5, 9). In keeping with the critical role of PML-RARα and/or the resident non-affected RARα allele, neither RARβ-((E)-3-Chloro-4-[2-(5,6-dihydro-5,5-dimethyl-8-phenyl-2-naphthalenyl) ethenyl]benzoic acid (Compound III)) nor RARβγ-(3-Fluoro-4[[(5,6,7,8-tetrahydro-5,5,8,8-tetramethyl-2-naphthalenyl) hydroxyacetyl]amino]benzoic acid (Compound IV)) selective retinoids induced differentiation as assessed by morphological criteria (FIG. 1a, top panel), NBT reduction (FIG. 1b, lanes 18, 20) and CD11c integrin expression (FIG. 1c, lanes 13, 15). That RAR pan-agonists induce NB4 maturation through RARα activation is also demonstrated by the observations that the RARα-selective antagonist 4-[[[5,6-Dihydro-5,5-dimethyl-8-(3-quinolinyl)-2-naphthalenyl]carbonyl]amino]benzoic acid (Compound II) decreased dramatically the maturation induced by 9-cis retinoic acid (9-cis RA) (FIG. 1b, lane 8; FIG. 1c, lane 6; similar data were obtained for ATRA, not shown). As expected the RARα agonist Compound I-induced differentiation was abrogated by Compound II or the RAR pan-antagonist (E)-4-[2-[8-(1,1'-Biphenyl]-4-yl)-5,6-dihydro-5, 5-dimethyl-2-naphthalenyl]ethenyl]benzoic acid (Compound VI) (FIG. 1b, lanes 13, 14; FIG. 1c, lane 10). In contrast to RAR agonists, RXR agonists (SR11237) alone were completely inactive (FIG. 1a, top panel; FIG. 1b, lane 23, FIG. 1c, lane 17; see also Kitamura, K. el al., *Leukemia* 11:1950–1956 (1997)).

Surprisingly, however, the SR11237 rexinoid agonist, which is devoid of any RAR activity (Chen, J. Y. et al., *Nature* 382:819–822 (1996); Lehmann, J. M. et al., *Science* 258:1944–1946 (1992)) induced full maturation of NB4 cells in the presence of the protein kinase A (PKA) agonist 8CPT-cAMP which on its own did not exhibit any differentiating activity. Morphological changes, CD 11c integrin expression and NBT reduction assays all demonstrated that the RXR-PKA crosstalk induced bonafide granulocytic maturation of NB4 cells as does ATRA (FIG. 1a, lower panel; FIG. 1b, lane 24, FIG. 1c, lane 18). Similar results were obtained with other rexinoid agonists (see below). Importantly, neither RARα-selective (Compound II) nor RAR pan-antagonists (Compound VI; identical results were obtained with other RAR pan-antagonists) affected significantly the RXR-PKA synergism for NB4 maturation, irrespective of whether 9-cis RA or SR11237 was used as RXR agonist (FIGS. 1b, c). This excludes any contribution of serum-borne traces of retinoic acid as well as unrecognized weak RAR agonist crossreactivity of SR11237, since RAR agonist-induced differentiation is efficiently inhibited by these antagonists (see above).

To provide additional evidence that it is not the RAR/RXR heterodimer whose PKA crosstalk induces differentiation, we took advantage of a recently discovered retinoid, 4-[1-[5,6-Dihydro-3,5,5-trimethyl-8-(1-methylethyl)-2-naphthalenyl]ethenyl]benzoic acid (Compound V; U.S. application Ser. No. 60/127,976, filed Apr. 6, 1999, titled "Selective Retinoic Acid Analogs"; and U.S. application Ser. No. 60/130,649, filed Apr. 22, 1999, titled "Selective Retinoic Acid Analogs". This retinoid has the rather exceptional characteristics that it acts as strong RXR AF-2 (GAL-RXRα, FIG. 2a) and RXR homodimer (FIG. 2b, lane 3) agonist on 17mer- and DR1-based reporters, respectively, while it is a pan-antagonist for RAR AF-2s (FIG. 2a), and nearly inactive with RAR-RXR heterodimers on a DR5-based reporter (FIG. 2b, lane 7). Despite being virtually inactive on its own, Compound V did not inhibit, but rather synergized with, ATRA-induced transactivation of such reporters (FIG. 2b, lane 8). In keeping with its inefficiency to activate the RAR/RXR heterodimer, Compound V alone did not exert any differentiative effect on NB4 cells (FIG. 2c). However, in presence of 8CPT-cAMP this retinoid induced maturation with a potency similar to 9-cis RA (FIG. 2c). Importantly, this activity was seen also in presence of a transactivation-incompetent RARα, as it could not be inhibited by RARα-selective (Compound II) or pan-antagonists (FIG. 2c).

Without being bound by any theory, based the above data, two distinct pathways exist for NB4 cells to undergo maturation. One involves RARα/RXR heterodimers and can be triggered by RARα agonists, while the second does not involve RAR-RXR heterodimers and depends on the crosstalk between RXR and PKA agonists. Monitoring cytokine signaling of NB4 cells by multiplex RNAse protection assays demonstrated that the two pathways do indeed trigger different gene programs. Most remarkably, the expression of G-CSF, which is weakly induced by the PKA agonist 8CPT-cAMP (FIG. 3a, lane 9), is dramatically boosted by SR11237 (lane 15), even though SR11237 on its own does not affect G-CSF expression (lanes 10–12). The factor of synergy was >50-fold, leading to a huge stimulation of G-CSF gene expression, which was undetectable in the non-induced state. Notably, ATRA was incapable of stimulating G-CSF expression (lanes 1–3), but induced the expressions of M-CSF (lane 3) and the C-X-C chemokine interferon-inducible protein 10 (IP10; FIG. 3b, lane 3), which were not seen with SR11237 and/or 8CPT-cAMP. GM-CSF expression was selectively triggered by the RXR-PKA crosstalk (FIG. 3a, lane 15) and SR11237 further stimulated 8CPT-cAMP induction of the expression of interleukin 8 (IL8), monocyte chemoattractant protein 1 (MCP I), and the C—C chemokines macrophage inflammatory proteins MIPla and MIPIP (FIG. 3b, lanes 9, 15). IL8 and MCPI expression was also induced by ATRA (lanes 2,3). Notably, some cytokines were induced by SR11237 on its own, as the c-kit ligand stem cell factor (SCF), IL8 and MCPI (FIG. 3a and b, lanes 11, 12). The only other tested condition leading to SCF induction was exposure to vitamin D3 (FIG. 3a, lanes 5, 6) which also induced IL8 expression (FIG. 3b, lanes 5, 6). The C—C cytokine RANTES which is constitutively expressed in NB4 cells is inhibited by the PKA agonist. This inhibition was compensated by coexposure to SR11237, leading only to a transient decrease at 24 h (compare lanes 7–9 with lanes 13–15).

That two distinct pathways can induce NB4 cell differentiation prompted us to test whether ATRA-resistant cells would still respond to the RXR-PKA crosstalk. Indeed, NB4-R2 cells (Ruchaud. S. et al., *Proc. Natl. Acad. Sci. USA* 91:8428–8432 (1994)), which are resistant to ATRA due to the mutation of $Gln_{411}$, to an in-phase stop codon in the ligand binding domain of PML-RARα (FIG. 4a), ceased growth in the presence of SR11237 or Compound V plus 8CPT-cAMP (note that NB4, but not NB4-R2, cells are growth inhibited by Compound I) and underwent granulocytic maturation, as confirmed by morphological criteria, NBT reduction (FIG. 4b), and CD11c integrin expression. Moreover, the rexinoid-PKA crosstalk induced the same pattern of cytokine expression in NB4 and NB4-R2 cells, whereas ATRA was unable to induce IP 10, MCP1 or M-CSF expression in the resistant cells, as it did in the parental NB4 cells (FIG. 3). No differentiation of NB4-R2 was seen in presence of the rexinoid or PKA agonists alone, nor in presence of ATRA or 9-cis RA (FIG. 4b). It is worth noting that, in presence of 8CPT-cAMP, Compound I induced some differentiation of NB4-R2 cells (lane 15), suggesting that the non-modified RARα allele can synergize with PKA agonists to induce some markers of differentiation even in the absence of morphological cell alterations (FIG. 4b, top panels).

RXR is a promiscuous heterodimerization partner for a great number of nuclear receptors (Mangelsdorf, D. J. et al, *Cell* 83:835–839 (1995); Gronemeyer, H. and Laudet, V., *Protein Profile* 2:1173–1308 (1995); Chambon, P., *FASEB J.* 10:940–954 (1996)) and NB4 differentiation could be potentially mediated by heterodimers other than RAR/RXR. To this end we tested thyroid hormone, vitamin D3 and PPAR agonists in presence of either the RXR agonist SR11237 or 8-CPT-cAMP. Only vitamin D3, which was inactive on its own and in the presence of SR11237, crosstalked at uM concentration with 8CPT-cAMP to produce a moderate granulocytic maturation, which was less than 20% of the effect exerted by SR11237 in presence of the PKA agonist. As none of the above heterodimers induced efficiently NB4 cell differentiation in response to the cognate ligand of the RXR partner when coexposed to 8CPT-cAMP, it is unlikely that the rexinoid acted through one of the above heterodimers. This is further supported by the apparently distinct gene programs initiated by vitamin D3 and the rexinoid-PKA agonist synergy (FIG. 3). No crosstalk between the PKA pathway was seen with rexinoid antagonists, such as the RXR-selective pan-antagonist HX531 (Vivat, V. et al., EMBO J. 16:5697–5709 (1997)), indicating that the synergism requires RXRs in a transcription-activating conformation.

Without being bound by any theory, it is concluded that NB4 cell differentiation can be achieved through two different signaling paradigms, i.e., either RARα agonists through RARα/RXR heterodimers or through rexinoid-PKA agonist synergism. (i) Due to "RXR subordination" the RAR/RXR heterodimer cannot respond to pure RXR agonists like SR11237 unless RAR is liganded (Lehmann, J. M. et al., Science 258:1944–1946 (1992); Vivat, V. et al., EMBO J. 16:5697–5709 (1997); Kurokawa, R. et al., Nature 3 71:528–531 (1994); Forman, B. M. et al., Cell 81:541–550 (1995)). In addition Compound V, which is a RXR homodimer agonist and RAR antagonist, was unable to efficiently activate RAR/RXR heterodimers on its own. (ii) However, together with the PKA agonist, but not on their own, both SR11237 and Compound V efficiently induced NB4 cell differentiation. Note that we have excluded that 8CPT-cAMP simply relieves "RXR subordination" in RAR/RXR heterodimers, since we did not observe any SR11237-induced transactivation of a DR5-based reporter by coexpressed RAR and RXR in presence of the PKA agonist. (iii) The cytokine/chemokine expression analysis confirms that SR11237 plus 8CPT-cAMP is not simply an alternative to induce the same signaling pathway as RARα agonists. (iv) Transgenic mice expressing a dominant negative RXR in myeloid cells exhibited maturation defects at the promyelocytic stage (Sunaga, S. et al., Br. J. Haematol. 96:19–30 (1997)) indicating that RXR is not just a silent heterodimerization partner of RAR and plays an active transcriptional role either in hetero- or homodimers which is crucial for myelopoiesis. (v) NB4 mutant cells which do not respond to ATRA do efficiently differentiate via the rexinoid-PKA pathway. Whether this RAR/RXR heterodimer-independent pathway operates by synergy between the PKA pathway and RXR homodimers or an as yet unidentified "RXR permissive" heterodimer remains to be established.

Importantly, the present data pave the way towards alternative therapies for APL patients to inhibit the outgrowth of ATRA-resistant pools of leukemic blasts and eliminate such cells from relapsed patients. The observations that (i) ATRA augments the expression levels of the receptors for G-CSF (Tkatch, L. S. et al., J. Leukoc. Biol. 57:964–971 (1995)) and GM-CSF (de Gentile, A. et al, Leukemia 8:1758–1762 (1994)), (ii) G-CSF and GM-CSF are superinduced by the PKA and rexinoid agonists (FIG. 3), and (iii) these cytokines combined with ATRA improve the haematological state of APL patients not previously receiving ATRA therapy (Usuki, K. et al., Int. J. Hematol. 64:213–219 (1996)), suggest that a combination therapy using retinoid, rexinoid and PKA agonists (or drugs elevating cAMP levels) can be more efficient than a plain therapy with ATRA and allow a less stringent chemotherapy, thereby reducing the risk of therapy-induced ATRA resistance. Chemotherapy can even become more efficient in G-CSF-inducing conditions, as treatment with recombinant G-CSF of a patient in the third relapse resistant to both cytotoxic drugs and ATRA sensitized the blasts to cell-cycle-dependent agents and led to complete remission (Katayama, N. et al., Am. J. Hematol. 58:31–35 (1998)).

Rexinoid-PKA agonist synergism can allow treatment of ATRA-resistant APL patients without involving toxic substances like arsenic trioxide (Chen, G. Q. et al., Blood 88:1052–1061 (1996); Soignet, S. L. et al., N. Engl. J. Med. 339:1341–1348 (1998)). It is shown herein that the ATRA resistance of NB4-R2, a cell line derived from a patient that was unsuccessfully treated by subsequent chemo- and ATRA therapy (Lanotte, M. et al., Blood 77:1080–1086 (1991); Duprez, E. et al., Leukemia 6:1281–1287 (1992)), is most likely due to a mutation in the ligand-binding domain of PML-RARα resulting in LBD truncation and the inability to bind ligand. Even though NB4-R2 cells are unresponsive to ATRA, they efficiently mature upon combined treatment with rexinoid (which in human clinical trials did not manifest side effects that are normally associated with retinoid therapy (Miller, V.A. et al., J. Clin. Oncol. 15:790–795 (1997))) and PKA agonists. PML-RARα LBD mutation is the main identified cause for ATRA resistance in patients and cell lines (Imaizumi, M. et al., Blood 92:374–382 (1998); Shao, W. et al., Blood 89:4282–4289 (1997); Kitamura, K. et al., Leukemia 11:1950–1956 (1997)) and it is likely that these resistant cells can be similarly differentiated as NB4-R2 cells upon treatment with rexinoid and PKA agonists. Towards this goal novel rexinoid agonists and modes of augmenting intracellular cAMP levels by stimulating cAMP synthesis or inhibiting phosphodiesterases, by applying synthetic cell-penetrating PKA agonists, such as the cAMP stereoisomer Sp-cAMPS, or by engineering tumor cell-targeted liposome-delivering drugs, will have to be tested for clinical use.

TABLE 1

| Ligand | RAR AF-2 | | | RYR AF-2 | (RXR)$_2$ DR1 | RARα-RXR DR5 |
|---|---|---|---|---|---|---|
| | α | β | γ | | | |
| ATRA | + | + | + | 0 | 0 | + |
| 9-cis RA | + | + | + | + | + | + |
| Compound I | + | 0 | 0 | 0 | 0 | + |
| Compound II | − | 0 | 0 | 0 | 0 | − |
| Compound III | 0 | + | 0 | 0 | nd | nd |
| Compound IV | 0 | (+) | + | 0 | 0 | 0 |
| Compound V | − | − | − | + | + | 0 |
| Compound VI | − | − | − | 0 | 0 | 0 |
| SR11237 | 0 | 0 | 0 | + | + | 0 |
| HX531 | 0 | 0 | 0 | − | − | 0 |

Figure 2A:
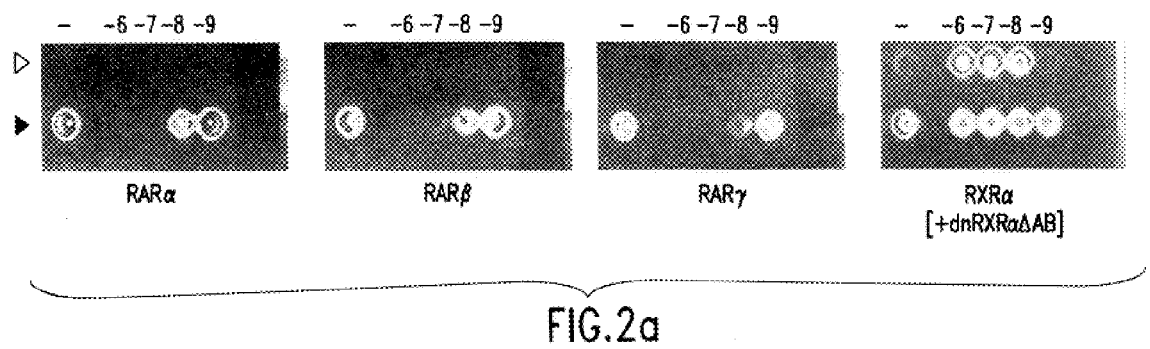
FIG. 2a. Reporter cell assays; the RAR and RXR AF-2 agonistic and antagonistic activities of 4-[1-[5,6-Dihydro-3,5,5-trimethyl-8-(1-methylethyl)-2-naphthalenyl]ethenyl]benzoic acid (Compound V) are displayed as false color illustration of the luciferase activity emanating after retinoid induction (from 1 μM, "−9" to 1 μM, "−6") from 96 well plates containing equal amounts of cells (Chen, J. Y. et al, *EMBO J.* 14:1187–1197 (1995)). Monitoring and quantitation was done by using a photon-counting camera. The open triangle points to signals in the presence of the retinoid (agonist activity; "−" indicates the signal for vehicle alone), the black triangle points to signals in the presence of both 10 nM ATRA ("−", only ATRA) and increasing amounts of the retinoid (antagonistic activity, if the ATRA-induced signal decreases). Note that the RXRα reporter cell line contains also the inactive dnRXRαΔAB, which lacks both AF-1 and AF-2, to sequester endogenous RARs that silence RXR in the absence of RAR agonists (Vivat, V. et al., *EMBO J.* 16:5697–5709 (1997)).
Figure 2B:
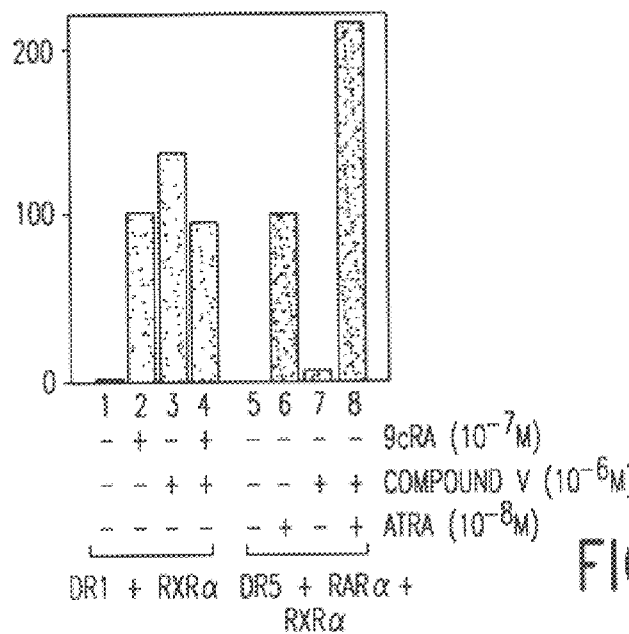
FIG. 2b. Transient transactivation of RXRA homodimers on a DR1 reporter in presence of 4-[1-[5,6-Dihydro-3,5,5-trimethyl-8-(1-methylethyl)-2-naphthalenyl]ethenyl]benzoic acid (Compound V) (relative to 0.1 μM 9-cis RA, standardized to 100) and of RARα-RXRα heterodimers (relative to 10 nM ATRA, standardized to 100). The small DR5 activation in FIG. 2b, lane 7, may originate from weak interaction of RXR homodimers with DR5 elements (Mader, S. et al., *J. Biol. Chem.* 268:591–600 (1993)).
Figure 2C:
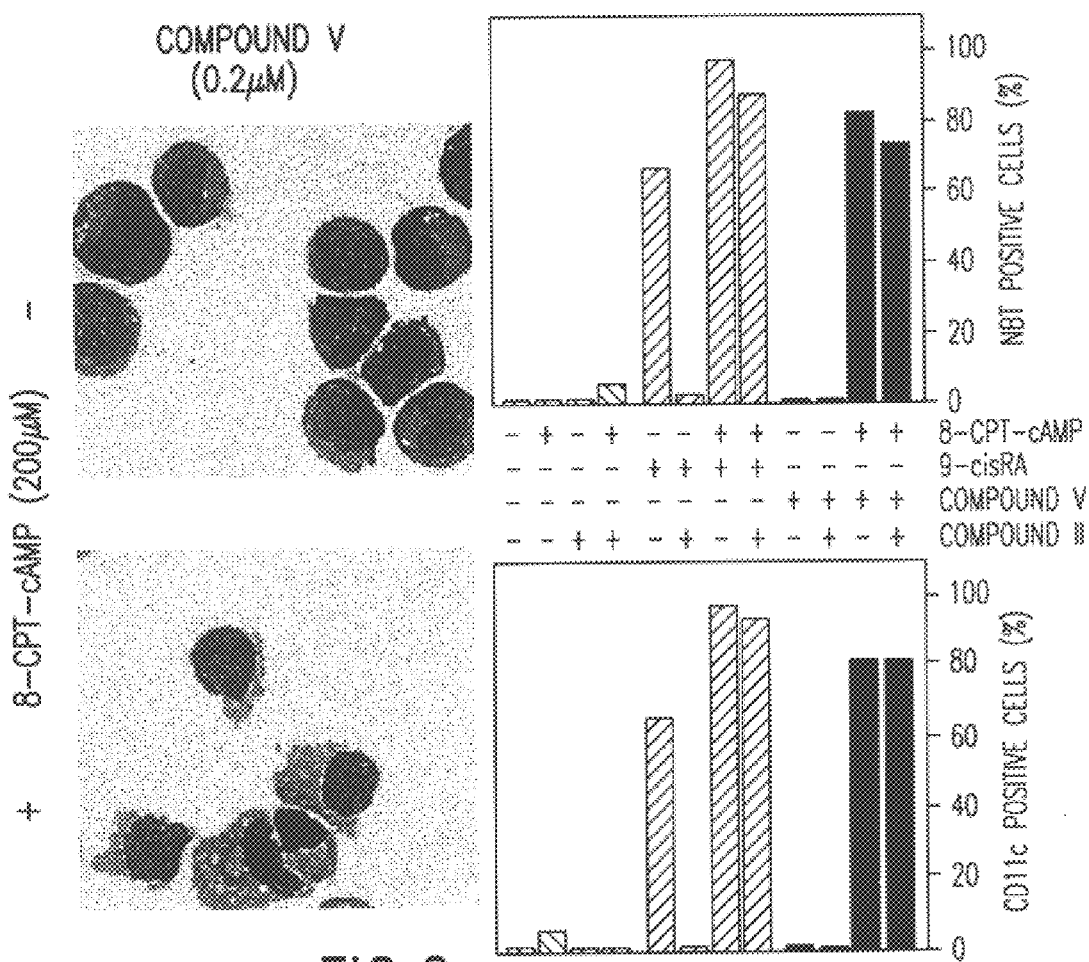
FIG. 2c. 4-[1-[5,6-Dihydro-3,5,5-trimethyl-8-(1-methylethyl)-2-naphthalenyl]ethenyl]benzoic acid (Compound V) is a highly potent partner of PKA signaling to trigger NB4 cell maturation. Morphological and histochemical features of NB4 cells treated with 4-[1-[5,6-Dihydro-3,5,5-trimethyl-8-(1-methylethyl)-2-naphthalenyl] ethenyl]benzoic acid (Compound V), with or without 8-CPT-cAMP as indicated. A comparative analysis of the synergistic action of 8-CPT-cAMP and 9-cis RA, 4-[[[5,6-Dihydro-5,5-dimethyl-8-(3-quinolinyl)-2-naphthalenyl]

The transcriptional activities of synthetic retinoids were determined for the AF2 functions of RARα, β, γ, and RXRα using reporter cells (see FIG. 2a and Chen, J.Y. el al., EMBO J. 14: 1187–1197 (1995)). RXRα homodimer activity on a DR1-tk-CAT or RARα-RXRα heterodimer activity on a DR5-tk-CAT reporter were assessed by transient RXR transfections. "+", agonist, "(+)", weak agonist, "−", antagonist, "0", no activity, "nd", not determined.

Materials and Methods

Retinoids. 4-[[(2,3-Dihydro-1,1,3,3-tetramethyl-2-oxo-1H-inden-5-yl)carbonyl]amino]benzoic acid (Compound I; WO 98/47861),4-[[[5,6-Dihydro-5,5-dimethyl-8-(3-quinolinyl)-2-naphthalenyl]carbonyl]amino]benzoic acid (Compound II; U.S. Pat. No. 5,559,248; U.S. Pat. No. 5,849,923), (E)-3-Chloro-4-[2-(5,6-dihydro-5,5-dimethyl-8-phenyl-2-naphthalenyl)ethenyl]benzoic acid (Compound III; U.S. Pat. No. 5,618,839), 3-Fluoro-4[[(5,6,7,8-tetrahydro-5,5,8.8-tetramethyl-2-naphthalenyl) hydroxyacetyl]aminolbenzoic acid (Compound IV; U.S. Pat. No. 5,624,957), 4-[1-[5,6-Dihydro-3,5,5-trimethyl-8-(1-methylethyl)-2-naphthalenyl]ethenyl]benzoic acid (Compound V; U.S. application Ser. No. 60/127,976, filed Apr. 6, 1999, titled "Selective Retinoic Acid Analogs"; and U.S. application Ser. No. 60/130,649, filed Apr. 22, 1999, titled "Selective Retinoic Acid Analogs", and (E)-4-[2-[8-(1,1'-Biphenyl]-4-yl)-5,6-dihydro-5,5-dimethyl-2-naphthalenyl]ethenyl]benzoic acid (Compound VI; WO98/46228) were obtained from Bristol-Myers Squibb.

The structures of (E)-3-Chloro-4-[2-(5,6-dihydro-5,5-dimethyl-8-phenyl-2-naphthalenyl)ethenyl]benzoic acid (Compound III) and 4-[1-[5,6-Dihydro-3,5,5-trimethyl-8-(1-methylethyl)-2-naphthalenyl]ethenyl]benzoic acid (Compound V) follow:

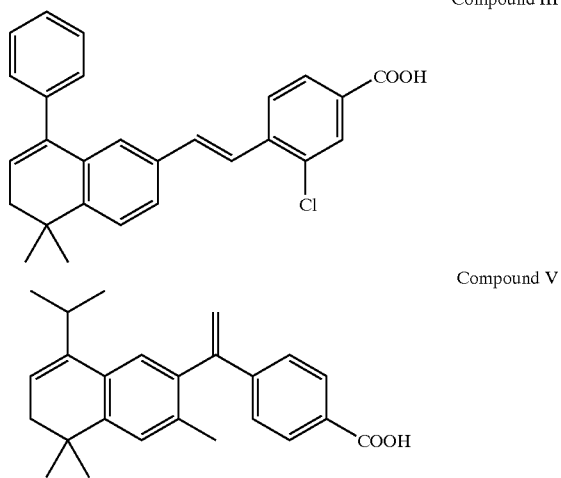

Compound III was synthesized by a method described in U.S. Pat. No. 5,618,839 using the following intermediate (X=Cl):

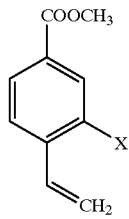

The above intermediate was synthesized from the commercially available 3-chloro-4-hydroxybenzoic acid as shown below:

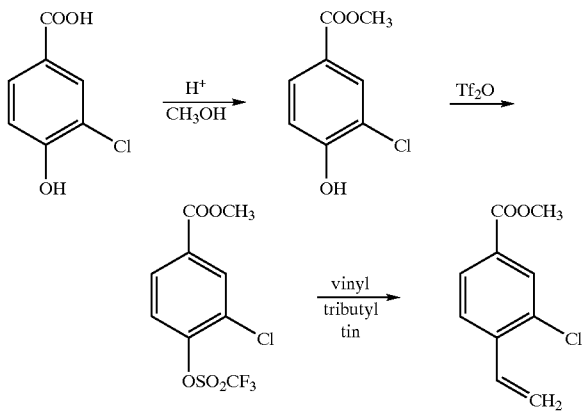

The acid was first esterified, followed by activation of the OH group with trifluoromethane sulfonic anhydride ($Tf_2O$), then the trifluoromethane sulfonate group was coupled with vinyl tributyl tin to give the desired intermediate.

Cells and cultures. NB4 and NB4-R2 cells were cultured as previously (Lanotte, M. et al., Blood 77:1080–1086 (1991)). Essentially, cultures were established with log phase growing cells at concentration ($10^5$ ocell per ml) allowing exponential growth of untreated control cultures over 3 days without medium replenishment. Retinoids (provided by Bristol-Myers Squibb; dissolved in ethanol as stock solution at $10^{-3}M$) and 8-CPT-cAMP (Sigma; dissolved in saline at $10^{-2}M$) were added at the indicated concentrations. Cultures were light-protected.

Morphological and functional cell maturation analysis. Cell morphology was analyzed after May-Grünwald staining. Histological NBT reaction was carried out as previously described (Lanotte, M. et al., Blood 77:1080–1086 (1991)). Morphology analysis and NBT reaction were performed after 72 h of treatment. At least 300 cells were analyzed for each treated culture. Data given are typical of one experiment, each treatment has been repeated at least three times.

Reporter cell assays. Synthetic retinoids were characterized using HeLa cells transfected with the corresponding GAL-RAR chimeras and the cognate $(17-mer)_5$-globin-luciferase reporter gene as described (Chen, J. Y. el al., EMBO J. 14:1187–1197 (1995)).

Flow cytometry analysis of CD11c cell surface integrin. The expression of CD11c integrin was analyzed by direct immunofluorescence, essentially as described (Ruchaud, S. et al., Proc. Natl. Acad. Sci. USA 91:8428–8432 (1994)). Briefly, after incubation (48 h), cells were washed in PBS and labeled with an anti-human CD11c FITC mouse monoclonal antibody (Becton-Dickinson). Cells were then washed twice in PBS and fixed in 1% paraformaldehyde/PBS solution. Cells were analyzed using a COULTER flow-cytometer.

RPA analysis. Total RNA was extracted with the Trizol reagent (Gibco BRL). The ribonuclease protection assay was performed according to the supplier's instructions (Pharmingen, San Diego, Calif.). Briefly, human cytokine 4 and 5 template sets (45034P; 45035P) were labeled with $\alpha$-$^{32}P$ uridine triphosphate. RNA (4 µg) and $6\times10^5$ cpm of labeled probes were used for hybridization. After RNAse treatments, the protected probes were resolved on a 5% urea-polyacrylamide-bis-acrylamide gel.

PML-RARα cDNA sequencing. Total RNA from NB4 and NB4-R2 cells was purified and PML-RARα specific mRNA was isolated using Dynal magnetic beads (M-280 streptavidin) coupled to a biotinylated PML-RARα oligonucleotide (specific for the sequence at the recombination site). This mRNA preparation was used for RT-PCR with oligod(N)6 as primer and AMV reverse transcriptase at 42° C. for 60 min. 1/20 of the RT reaction was used for PCR amplification with the primers R2L (CTG CCC CTG GAG ATG GAT GAT) (SEQ ID NO:1) and R2H (GCG GAG GGC GAG GGC TGT GTC) (SEQ ID NO:2) and the following conditions: 5 min at 95° C., cycle 1 min 95° C., 2 min 65° C., 1 min 30 sec 72° C., and then 0 min 72° C. The PCR product was gel isolated and cloned into the pCR™2.1 AT sequencing vector. Clones were selected and PCR-tested for the presence of the insert. Positive clones were selected, plasmids were purified from these clones and DNA was sequenced with SP6 and T7 primers using the Perkin Elmer Big Dye kit and ABI 377 automatic sequencer.

Example 2

Effect of RXR ligand on cell lipid accumulation was evaluated in human breast cancer cell line T47D in the absence or presence of 100 pM cAMP analog (8CPT-cAMP) (FIG. 5). Cells were treated with RXR alone (blue bars) and RXR+ 100 µM of 8CPT-cAMP (red bars) for 7 days and stained for lipid accumulation by Nile Red (fluorescent lipid staining dye). Addition of CPT-cAMP increased differentiation of T47D breast cancer cells over RXR ligands alone by 20% at 1 μM SR11237 and bexarotene. No effect was observed in the presence of 100 μM CPT-cAMP alone. $EC_{50}$ for lipid accumulation for RXR compound alone treated cells was 62 nM (bexarotene) and 110 nM (SR11237). Addition of CPT-cAMP did not increase the sensitivity of T47D to differentiation by RXR compounds. These results demonstrate that activating the cAMP pathway can increase the differentiation response in breast cancer cells to RXR ligand. This biological strategy may serve as a viable combination therapy for the treatment of solid tumor cancers of epithelial origin.

Materials and Methods

Nile Red Staining Method

Reagents. Fixing solution: 1.5% glutaraldehyde in PBS. Staining Solution: Stock Solution (1 mg Nile red and 1 ml acetone were mixed thoroughly and stored, chilled and protected from light). Working Solution: 4 ul stock solution was added to I ml of 75% glycerol (PBS) followed by briefly vortexing; the dye solution was then briefly degassed by vacuum to remove bubble.

Fixation. Slides were covered with 1.5% glutaraldehyde for 5 minutes and then washed with buffered saline.

Staining. For Fluorescence Microscope, a drop of dye-glycerol solution was added to a slide and covered with a glass coverslip. After 5 minutes, the slide was viewed by fluorescence microscope, Excitation 450–500 nm, Emission>528 nm. For Flow Cytofluorometry, the medium was aspirated off from cells and washed with PBS two times (serum in the medium drained the dye out of the cells). Then the cells were trypsinized and washed with PBS to get rid of trypsin. The cells were spun down and resuspended in 1 ml PBS ($1-2\times10^6$/ml). The stock dye was added directly to the cells suspension in PBS with 1:100 dilution, and incubated at room temperature for a minimal of 5 minutes, and the samples were analyzed immediately. For Fluorescence Spectra, the medium was removed from 96-well plates and the cells were washed once with PBS. The cells were fixed with 1.5% glutaraldehyde for 5 minutes, then washed with PBS (cells can be unfixed). Diluted dye in PBS (1:100 from stock) was added to the cells, incubated for 5 minutes, and the plate was read at Excitation 488nm with a 2-nm slit width, emission at 540 nm with a 20-nm slit width.

Cells. Breast cancer cell line T47D was obtained from American Type Culture Collection, Manassas, Va. See, Freake et al., *Biochem. Biophys. Res. Comm.* 101:1131–1138 (1981), and Sheret al., *Biochem. J.* 200:315–320 (1981).

Example 3

Preparation of 4-[1-(5,6-Dihydro-3,5,5-trimethyl-8-isopropyl-2-naphthalenyl)ethenyl]benzoic Acid (Compound V)

Synthesis Scheme

1) Preparation of 1,2,3,4-tetrahydro-4,4,6-trimethyl-7-bromo-1-oxo-naphthalene

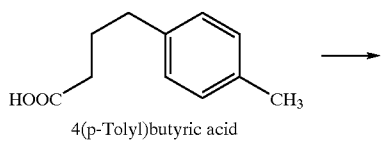

4(p-Tolyl)butyric acid

-continued

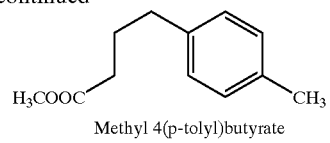

Methyl 4(p-tolyl)butyrate

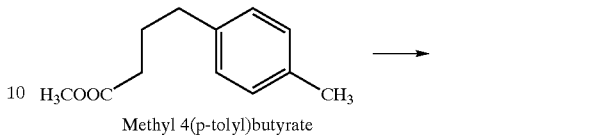

Methyl 4(p-tolyl)butyrate

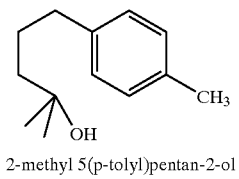

2-methyl 5(p-tolyl)pentan-2-ol

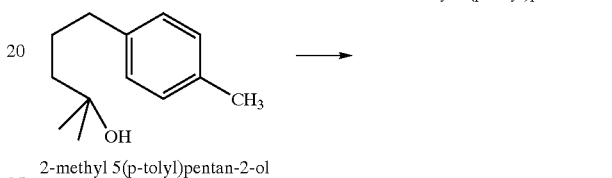

2-methyl 5(p-tolyl)pentan-2-ol

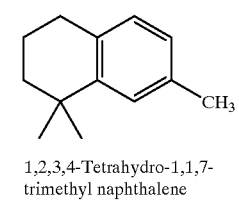

1,2,3,4-Tetrahydro-1,1,7-trimethyl naphthalene

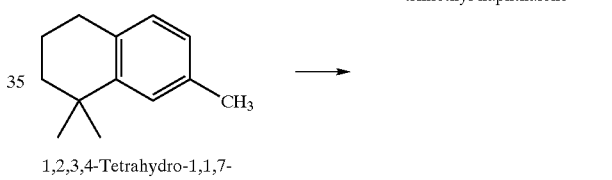

1,2,3,4-Tetrahydro-1,1,7-trimethyl naphthalene

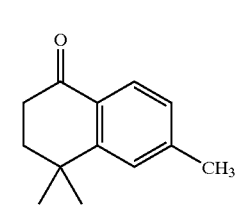

1,2,3,4-Tetrahydro-4,4,6-trimethyl-1-oxo-naphthalene

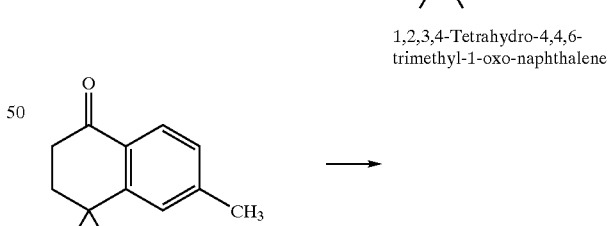

1,2,3,4-Tetrahydro-4,4,6-trimethyl-1-oxo-naphthalene

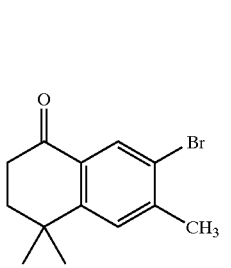

1,2,3,4-Tetrahydro-4,4,6-trimethyl-7-bromo-1-oxo-naphthalene

2) Preparation of ethyl 4(1(tributylstannyl)-2-(trimethylsilyl)-ethen-1-yl)-benzoate

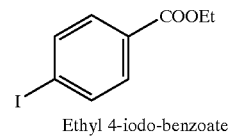
Ethyl 4-iodo-benzoate

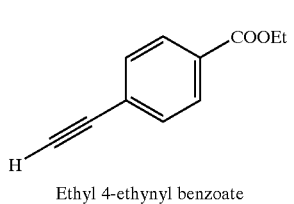
Ethyl 4-ethynyl benzoate

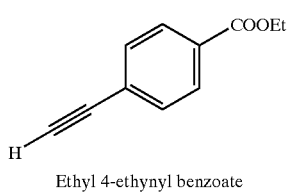
Ethyl 4-ethynyl benzoate

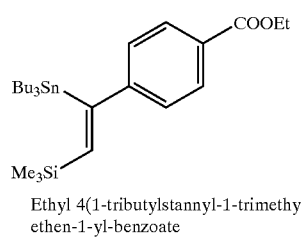
Ethyl 4(1-tributylstannyl-1-trimethyl-silyl)-ethen-1-yl-benzoate

3) Preparation of 4[1(5,6-dihydro-3,5,5-trimethyl-8-isopropyl-2-naphthalenyl)ethenyl]-benzoic acid

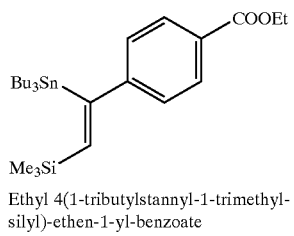
Ethyl 4(1-tributylstannyl-1-trimethyl-silyl)-ethen-1-yl-benzoate

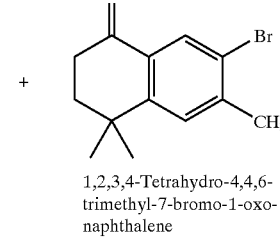
1,2,3,4-Tetrahydro-4,4,6-trimethyl-7-bromo-1-oxo-naphthalene

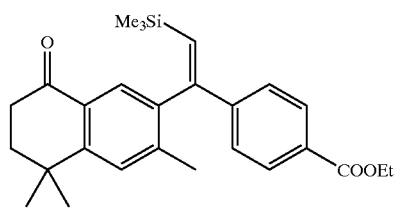
Ethyl 4[1(5,6,7,8-tetrahydro-3,5,5-trimethyl-8-oxo-2-naphthalenyl)-2-trimethylsilyl-ethenyl]benzoate

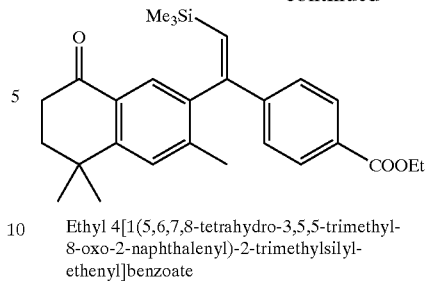
Ethyl 4[1(5,6,7,8-tetrahydro-3,5,5-trimethyl-8-oxo-2-naphthalenyl)-2-trimethylsilyl-ethenyl]benzoate

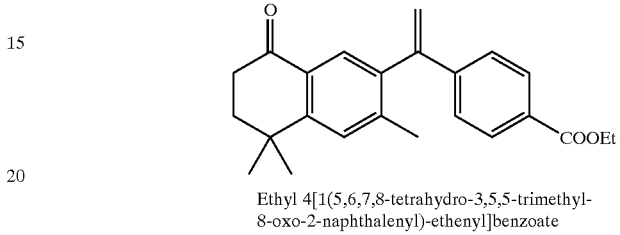
Ethyl 4[1(5,6,7,8-tetrahydro-3,5,5-trimethyl-8-oxo-2-naphthalenyl)-ethenyl]benzoate

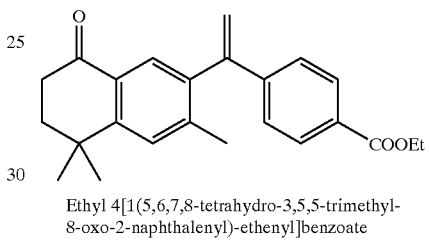
Ethyl 4[1(5,6,7,8-tetrahydro-3,5,5-trimethyl-8-oxo-2-naphthalenyl)-ethenyl]benzoate

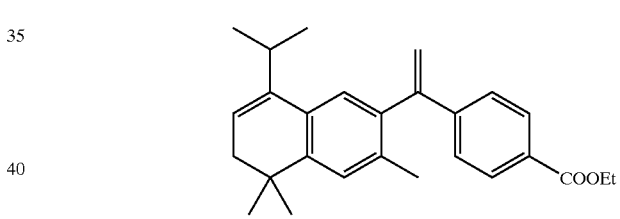
Ethyl 4[3,5,5-trimethyl-5,6-dihydro-8-isopropyl-2-naphthalenyl)-ethenyl]benzoate

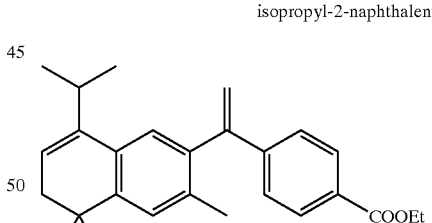
Ethyl 4[3,5,5-trimethyl-5,6-dihydro-8-isopropyl-2-naphthalenyl)-ethenyl]benzoate

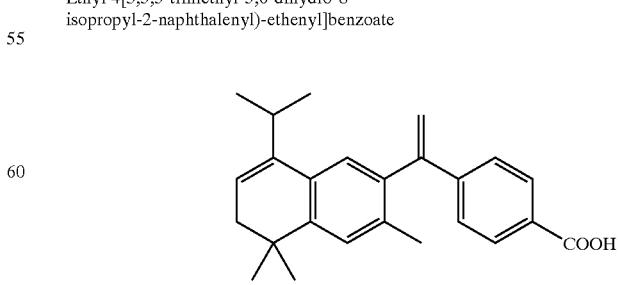
4-[1(5,6-Dihydro-3,5,5-trimethyl-8-isopropyl-2-naphthalenyl)ethenyl]benzoic acid

1. Preparation of 1,2,3,4-Tetrahydro-4,4,6-trimethyl-7-bromo-1-oxo-naphthalene Methyl 4-(p-tolyl)-butyrate A solution of 4-(p-tolyl)-butyric acid (10.0 g, 56.11 mmol) in methanol (680 mL) was treated with concentrated sulfuric acid (5.4 mL). The reaction was stirred at room temperature for 18 hour. Sodium bicarbonate ($\approx$15 g) was added and the mixture was stirred for 15 minutes, then concentrated. The residue was dissolved in ethyl acetate/water. The organic phase was separated and washed with brine, dried over anhydrous magnesium sulfate, filtered and concentrated to give the title material (10.8 g, 100% crude) as an oil which was used for the next reaction.

$^1$H NMR 400 MHz (CDCl$_3$) δ (ppm): 7.11 (2H, d, J$_{AB}$=8.2 Hz, H-2 and H-6), 7.03 (2H, d, J$_{AB}$=8.2 Hz, H-3 and H-5), 3.68 (3H, s, —OCH$_3$), 2.62 (2H, t, J=7.5 Hz, —CH$_2$—CO$_2$Me), 2.34 (2H, t, J=7.5 Hz, Ar—CH$_2$—), 2.33 (3H, s, —CH$_3$), 1.95 (2H, qi, J=7.5 HZ, —CH$_2$—CH$_2$—CH$_2$—).

2-Methyl-5-(p-tolyl)-pentan-2-ol

A solution of methyl 4-(p-tolyl)-butyrate (10.8 g, 56.2 mmol) in ether (215 mL) and benzene (215 mL) was treated dropwise ($\approx$15 minutes) with methylmagnesium bromide (3M in ethyl ether, 45 mL, 135 mmol). The mixture was stirred at room temperature for 1.5 hours, then cooled down to 0° C. and treated with 10% aqueous ammonium chloride (100 mL). The pH was then adjusted to 6.5–7 with concentrated hydrochloric acid and the mixture was diluted with ethyl acetate ($\approx$200 mL). The organic phase was separated and washed with brine/water 1:1, brine, dried over anhydrous magnesium sulfate, filtered and concentrated to give the title material (10.4 g, 96%) as a yellowish oil which was used for the next reaction. $^1$H NMR 400 MHz (CDCl$_3$) δ (ppm): 7.10 (4H, s, H-2, H-3, H-5 and H-6), 2.60 (2H, t, J=7.6 Hz, Ar-CH$_2$-), 2.33 (3H, s, Ar—CH$_3$), 1.73–1.65 and 1.54–1.50 (2×2H, 2m, —CH$_2$—CH$_2$—), 1.22 (6H, s, 2×—CH$_3$).

1,2,3,4-Tetrahydro-1,1,7-trimethyl-naphthalene

A solution of 2-methyl-5-(p-tolyl)-pentan-2-ol (10.4 g, 54.1 mmol) in ethyl ether (100 mL) at 0° C. was treated with concentrated sulfuric acid (64 mL). The mixture was stirred at 0° C. for 1.5 hours, and then poured into a mixture of ice/water. The mixture was diluted with ethyl ether, the organic phase was separated, washed with water (2×), saturated sodium bicarbonate and brine. The aqueous phase was extracted with ethyl ether and combined organic extracts were dried over anhydrous magnesium sulfate, filtered and concentrated to give the title material (9.6 g, 100% crude) as a yellowish oil which was used for the next reaction.

$^1$H NMR 400 MHz (CDCl$_3$) δ (ppm): 7.14 (1H, br s, H-8), 6.96 (2H, d, J=7.7 Hz, H-5), 6.91 (1H, br d, J=7.7 Hz, H-6), 2.74 (2H, t, J=6.3 Hz, H-4), 2.32 (3H, s, —CH$_3$-7), 1.83–1.77 and 1.68–1.65 (2×2H, 2m, H-3 and H-2), 1.29 (6H, s, 2×—CH$_3$-1).

1,2,3,4-Tetrahydro-4,4,6-trimethyl-1-oxo-naphthalene

A solution of 1,2,3,4-tetrahydro-1,1,7-trimethyl-naphthalene (9.60 g, 55 mmol), potassium bromate (9.17 g, 55 mmol), cerium ammonium nitrate (1.50 g) in water (28 mL) and dioxane (44 mL) was heated under argon at 85° C. for 6 hours. The mixture was then cooled down to 0° C., diluted with ethyl acetate and water. The organic phase was separated and the aqueous phase was extracted with ethyl acetate. The combined organic extracts were washed with water (2×), saturated sodium bicarbonate and brine, dried over anhydrous magnesium sulfate, filtered and concentrated. The residue was purified by silica gel chromatography (6.5×17 cm, 10% ethyl acetate/hexane) to give the title material (9.2 g, 89%) as a colorless oil.

IR (film) $\nu_{max}$ (cm$^{-1}$): 2940, 2910, 2840, 1670 (C=O), 1600. $^1$H NMR 400 MHz (CDCl$_3$) δ (ppm): 7.94 (1H, d, J=8.0 Hz, H-8), 7.22 (1H br s, H-5), 7.12 (1H, dd, J=8.0 and 0.8 Hz, H-7), 2.71 (2H, t, J=6.8 Hz, H-2), 2.41 (3H, s, —CH$_3$-6), 2.02 (2H, t, J=6.8 Hz, H-3), 1.39 (6H, s, 2×—CH$_3$-4). MS DCl: 189 (MH)$^+$.

1,2,3,4-Tetrahydro-4,4,6-trimethyl-7-bromo-1-oxo-naphthalene To a stirred suspension of aluminum trichloride (1.1 g, 8.1 mmol) in dichloromethane (2.5 mL) was added a solution of 1,2,3,4-tetrahydro-4,4,6-trimethyl-1-oxo-naphthalene (0.564 g, 3 mmol) in dichloromethane (1 mL) at 0° C. The mixture was stirred at this temperature for 45 minutes and then at room temperature for 45 more minutes. Bromine (0.185 mL, 3.6 mmol) was then added and the resulting mixture was stirred 2 hours at room temperature. The mixture was poured into a mixture of ice (50 mL), concentrated hydrochloric acid ($\approx$15 mL) and ethyl ether ($\approx$50 mL). The organic phase was separated and washed with IN hydrochloric acid, saturated sodium bicarbonate, aqueous sodium thiosulfate and brine. The aqueous phases were extracted with ethyl ether and the combined organic extracts were dried over anhydrous magnesium sulfate, filtered and concentrated. The residue was purified by silica gel chromatography (2.5×17 cm, 0 to 5% ethyl acetate/toluene) to give the title material which was triturated in cold hexane (0.700 g, 87%).

IR (KBr) $\nu_{max}$ (cm$^{-1}$); 2960, 2930, 2860, 1675 (C=O). $^1$H NMR 400 MHz (CDCl$_3$) δ ppm): 8.17 (1H s, H-8), 7.28 (1H s, H-5), 2.72 (2H, t, J=6.8 Hz, H-2), 2.02 (3H, s, —CH$_3$-6), 2.01 (2H, t, J=6.8 Hz, H-3), 1.38 (6H, s, 2×—CH$_3$-4). Anal. Calcd. for C$_{13}$H$_{15}$BrO: C, 58.44; H 5.66. Found: C, 58.12; H, 5.78.

Preparation of Ethyl 4-(1-(Tributylstannyl)-2-(trimethylsilyl)-ethen-1-yl)-benzoate

Ethyl 4-Ethynyl-benzoate

A solution of ethyl 4-iodo-benzoate (55.2 g, 0.2 mol) in triethylamine (800 mL) was purged with argon. Copper iodide (1.1 g) and bis(triphenylphosphine)palladium(II) dichloride (7.0 g) were then added and the mixture was purged again. Trimethylsilylacetylene (42 mL, 0.3 mol) was then added at 0° C. for 30 minutes and the resulting mixture was stirred at room temperature for 1 hour. The mixture was concentrated, triturated in hexane and filtered. The filtrate was concentrated to give ethyl 4-(2-trimethylsilylethen-1-yl)-benzoate (51.5 g, 100% crude) as a black oil.

$^1$H NMR 400 MHz (CDCl$_3$) δ (ppm): 7.98 (2H, d, J=8.4 Hz, H-2 and H-6), 7.52 (2H, d, J=8.4 Hz, H-3 and H-5), 4.38 (2H, qa, J=7.1 Hz, —OCH$_2$—), 1.40 (3H, t, J=7.1 Hz, —CH$_3$), 0.27 (9H, s, —Si(CH$_3$)$_3$).

The crude material was diluted in ethanol (500 mL) and potassium carbonate (2.4 g) was added. The resulting mixture was stirred overnight at room temperature. The mixture was concentrated and the residue was triturated in hexane and filtered. The filtrate was concentrated and the residue was purified by Kugelrohr distillation ($\approx$0.1 mm Hg, bath $\approx$70–80° C.) and afforded the title material (27.2 g, 78%) as a colorless oil which solidifies.

IR (KBr) $\nu_{max}$ (cm$^{-1}$): 3300 (≡C—H), 2980. 2940, 2910, 2110 (—C≡C—), 1715 (C=O). $^1$H NMR 400 MHz (CDCl$_3$) δ (ppm): 8.01 (2H, d, J=8.2 Hz, H-2 and H-6), 7.56 (2H, d, J=8.2 Hz, H-3 and H-5), 4.40 (2H, qa, J=7.1 Hz, —OCH$_2$—), 3.24 (1H, s, ≡C—H), 1.41 (3H, t, J=7.1 Hz, —CH$_3$).

Ethyl 4-(1-(Tributylstannyl)-2-(trimethylsilyl)-ethen-1-yl)-benzoate

A mixture of ethyl 4-ethynyl-benzoate (27.0 g, 0.155 mol), trimethylsilyltributyltin (65 mL. 0.186 mol), tetrakis(triphenylphosphine) palladium(0) (2.9 g) in dioxane (270 mL) was purged with argon, and then heated to 85° C. for 1.5 hours. The mixture was cooled down to room temperature and concentrated. The residue was purified by silica gel pad chromatography (10.5×15 cm, 0 to 5% ethyl acetate/hexane) to give the title a slightly yellowish oil. $^1$H NMR 400 MHz (CDCl$_3$) δ (ppm): 7.95 (2H, d, J=8.2 Hz, H-2 and H-6), 7.03 (2H, d, J=8.3 Hz, H-3 and H-5), 6.57 (1H s, ethenyl H), 4.38 (2H, qa, J=7.1 Hz, —OCH$_2$—),1.41 (3H, t, J=7.1 Hz, —OCH$_2$CH$_3$),1.41 (6H, m, 3x—CH$_2$—),1.26 m, J=7.3 Hz, 3x—CH$_2$—CH$_2$—CH$_3$), 0.91 (6H, m, 3x—SnCH$_2$—), 0.86 (9H, t, J=7.3 Hz, 3x—CH$_2$—CH$_3$), 0.19 (9H, s, —Si(CH$_3$)$_3$).

3. Preparation of 4-[1-(5,6-Dihydro-3,5,5-trimetltyt-8-isopropyl-2-naphthalenyl)ethenyl]benzoic Acid Ethyl 4-[1-(5,6,7,8-Tetrahydro-3,5,5-trimethyl-8-oxo-2-naphthalenyl)-2-trimethylsilyl-ethenyl]benzoate A solution of 1,2,3,4-tetrahydro-4,4,6-trimethyl-1-oxo-7-bromo-naphthalene (8.5 g, 31.8 mmol) was purged with argon (2x). Lithium chloride (4.0 g), copper iodide (0.860 g), tetrakis(triphenylphosphine)palladium(0) (1.8 g, 1.6 mmol) and ethyl 4-(1-(tributylstannyl)-2-(trimethylsilyl)-ethen-1-yl)-benzoate (24.0 g, 44.5 mmol) were then added and the resulting mixture was again purged with argon. The mixture was heated to 80° C. for ≈4 hours, and then cooled down to room temperature. The mixture was poured into cold water (1L) and was diluted with ethyl ether. The organic phase was separated, washed with cold water (2×lL), saturated sodium bicarbonate (1L), brine, dried over anhydrous magnesium sulfate, filtered and concentrated. The residue was purified by silica gel chromatography (8×15 cm, 0 to 5% ethyl acetate/toluene) to give the title material which was triturated in hexane (12.2 g, 88%).

$^1$H NMR 400 MHz (CDCl$_3$) δ (ppm): 7.94 (2H, d, J=8.3 Hz, H-2 and H-6), 7.85 (1H, s, H-1'), 7.31 (2H, d, J=8.3 Hz, H-3 and H-5), 7.22 (1H s, H-4'), 6.53 (1H, s, ethenyl H), 4.37 (2H, qa, J=7.1 Hz, —OCH$_2$—), 2.76 (2H, t, J=6.7 Hz, H-7'), 2.03 (2H, t overlapped by —CH$_3$-3', H-6'), 2.03 (3H, s, —CH$_3$-3'), 1.43 (6H, br s, 2x—CH$_3$-5'), 1.39 (3H, t, J=7.1 Hz, —CH$_2$—CH$_3$), −0.17 (9H, s, —Si(CH$_3$)$_3$)$_3$). Anal. Calcd. for C$_{27}$H$_{34}$O$_3$Si: C, 74.61; H, 7.89. Found: C, 75.08; H, 7.94.

Ethyl 4-1-(5,6,7,8-Tetrahydro-3,5,5-trimethyl-8-oxo-2-naphthalenyl)-ethenyl]benzoate A solution of ethyl 4-[1-(5,6,7,8-tetrahydro-3,5,5-trimethyl-8-oxo-2-naphthalenyl)-2-trimethylsilyl-ethenyl]benzoate (12.0 g, 27.6 mmol) in dichloromethane (900 mL) was treated with trifluoroacetic acid (100 mL) at 0° C. The mixture was stirred for 18 hours and allowed to reach room temperature. The mixture was diluted with toluene (≈100 mL) and concentrated. The residue was purified by silica gel chromatography (8×15 cm, 0 to 5% ethyl acetate/toluene) and gave the title material as a yellowish solid which was triturated in hexane (9.7 g, 97%). An analytical sample was recrystallized in hexane.

IR (KBr)ν$_{max}$ (cm$^{-1}$): 2970, 2950, 2910, 2875, 1712 and 1685 (C=O), 1605. $^1$H NMR 400 MHz (CDCl$_3$) δ (ppm): 7.97 (2H, d, J=8.4 Hz, H-2 and H-6), 7.91 (1H s, H-1'), 7.31 (2H, d, J=8.4 Hz, H-3 and H-5), 7.22 (1H, s, H-4'), 5.86 (1H, d, J=0.6 Hz, ethenyl H), 5.35 (1H br s, ethenyl H), 4.38 (2H, qa, J=7.1 Hz, —OCH$_2$—), 2.76 (2H, t, J=6.8 Hz, H-7'), 2.05 (3H, s, —CH$_3$-3'), 2.07-2.04 (2H, t overlapped by —CH$_3$-3', H-6'), 1.43 (6H, s, 2x—CH$_3$-5'), 1.40 (3H, t, J=7.1 Hz, —CH$_2$—CH$_3$). Anal. Calcd. for C$_{24}$H$_{26}$O$_3$: C, 79.53; H, 7.23. Found: C, 79.26; H, 7.30.

Ethyl 4-[(3,5,5-Trimethyl-5,6-dihydro-8-isopropyl-2-naphthalenyl)ethenyl]benzoate In a three-necked flask, cerium(III) chloride heptahydrate (13.5 g, 35 mmol) was dried for 2 hours at ≈145° C. under vaccum (for more details on the drying procedure, see *J. Am. Chem. Soc.* 111:4392–4398 (1989)). While still hot, argon was introduced and the flask was cooled to 0–5° C. and tetrahydrofuran (120 mL) was quickly added with vigorous stirring. The ice-bath was removed and the solution was stirred overnight (≈18 h) at room temperature. The solution was then cooled down to 0–5° C. again and isopropyl magnesium chloride (12 mL of 3M solution in ethyl ether) was added dropwise and the mixture was vigorously stirred for 1.5 hours. A solution of Ethyl 4-[1-(5,6,7,8-tetrahydro-3,5,5-trimethyl-8-oxo-2-naphalenyl)-ethenyl]benzoate (prepared above) (9.06 g, 25 mmol) in tetrahydrofuran (15 mL) was then added dropwise to this mixture and the resulting mixture was stirred for 45 minutes at 0–5° C. Acetic acid (10%, 100 mL) was slowly added and the mixture was extracted with ethyl ether (≈100 mL). The organic phases were washed with water, saturated sodium bicarbonate and brine, dried over anhydrous magnesium sulfate, filtered and concentrated. The residue was purified by silica gel chromatography. The title material was obtained (6.1 g, 63%) as a white solid along with the starting material (1.0 g, 11%) and ethyl 4-[(3,5,5-trimethyl-5,6-dihydro-8-hydroxy-2-naphthalenyl)ethenyl]benzoate (1.0 g, 11%).

IR (KBr) ν$_{max}$ (cm$^{-1}$): 2970, 2960, 2950, 2920, 2870, 1710 (C=O), 1605. $^1$H NMR 400 MHz (CDCl$_3$) δ ppm): 7.98 (2H, d, J=8.3 Hz, H-2 and H-6), 7.37 (2H, d, J=8.3 Hz, H-3 and H-5), 7.18 and 7.12(2×1H 2s, H-1' and H-4'), 5.85 (1H br s, ethenyl H), 5.77 (1H t, J=4.6 Hz, H-7'), 5.35 (1H, br s, ethenyl H), 4.38 (2H, qa, J=7.1 Hz, —OCH$_2$—), 2.95 (1H m, J=6.7 Hz, —CH(CH$_3$)$_2$), 2.22 (2H, d, J=4.6 Hz, H-6'), 2.01 (3H, s, —CH$_3$-3'), 1.40 (3H, t, J=7.1 Hz, —CH$_2$—CH$_3$), 1.27 (6H, s, 2x—CH$_3$-5'), 1.16 (6H, d, J=6.8 Hz, —CH(CH$_3$)$_2$). Anal. Calcd. for C$_{27}$H$_{32}$O$_2$: C, 83.46; H, 8.30. Found: C, 83.27; H, 7.67.

4-[1-(5,6-Dihydro-3,5,5-trimethyl-8-isopropyl-2-naphthalenyl)ethenyl]benzoic Acid A solution of Ethyl 4-[(3,5,5-trimethyl-5,6-dihydro-8-isopropyl-2-naphthalenyl)ethenyl]benzoate (3.9 g, 10 mmol) was saponified by dropwise treatment with sodium hydroxide (10N) and stirred at room temperature. The solution was cooled down to 0–5° C. and IN HCl was added dropwise with vigorous stirring. After stirring, the resulting white precipitate was filtered, washed with water and dried. After work-up, the title compound (3.1 g, 86%) was afforded as a white solid.

IR (KBr) ν$_{max}$ (cm$^{-1}$): 3330–2300 (br), 1690 (C=O), 1605. $^1$H NMR 400 MHz (DMSO-d$_6$) δ (ppm): 7.90 (2H, d, J=8.4 Hz, H-2 and H-6), 7.36 (2H, d, J=8.4 Hz, H-3 and H-5), 7.18 and 7.08 (2×1H, 2 s, H-1' and H-4'), 5.96 (1H, s, ethenyl H), 5.75 (1H t, J=4.4 Hz, H-7'), 5.32(1H, s, ethenyl H), 2.89 (1H m, J=6.7 Hz, —CH(CH$_3$)$_2$), 2.15 (2H, d, J=4.3 Hz, H-6'), 1.96 (3H, s, —CH$_3$-3'), 1.21 (1H, s, 2x—CH$_3$-5'), 1.09 (6H, d, J=6.7 Hz, —CH(CH$_3$)$_2$). Anal. Calcd. for C$_{25}$H$_{28}$O$_2$: C, 83.29; H, 7.83. Found: C, 83.24; H, 8.37.

All documents, e.g., scientific publications, patents and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method of treating leukemia in a subject, said method comprising:
   (a) administering to said subject a pharmaceutically effective amount of a retinoid X receptor (RXR)-selective agonist; and
   (b) administering to said subject a pharmaceutically effective amount of an agent which is capable of activating protein kinase A (PKA).

2. The method of claim 1, further comprising (c) administering to said subject a pharmaceutically effective amount of a retinoic acid receptor agonist (RAR).

3. The method of claim 1, further comprising administering to said subject a pharmaceutically effective amount of a cytokine selected from the group consisting of a granulocyte colony-stimulating factor (G-CSF), a granulocyte macrophage colony-stimulating factor (GM-CSF), a macrophage colony-stimulating factor (M-CSF), interleukin 8 (IL8), monocyte chemoattractant protein 1 (CP1), macrophage inflammatory protein MIP1α, and macrophage inflammatory protein MIP1β.

4. The method of claim 1, wherein said leukemia is acute promyelocytic leukemia (APL).

5. The method of claim 4, wherein said APL is resistant to treatment with a retinoic acid receptor (RAR) a agonist.

6. The method of claim 1, wherein said RXR-selective agonist is selected from the group consisting of 9-cis retinoic acid, bexarotene, 4-[1-[5,6-Dihydro-3,5,5-trimethyl-8-(1-methylethyl)-2-naphthalenyl]ethenyl]benzoic acid, and SR11237.

7. The method of claim 1, wherein said agent is a PKA agonist.

8. The method of claim 7, wherein said PKA agonist is selected from the group consisting of 8-bromo-cAMP, Sp-cAMPS, 8CPT-cAMP, dibutyryl-cAMP, Sp-5,6-DCl-cBiMPS, adenylate cyclase toxin, forskolin, L-858051, and Sp-8-pCPT-cGMPS.

9. The method of claim 1, wherein said agent is a compound which increases cAMP level.

10. The method of claim 9, wherein said compound stimulates cAMP synthesis.

11. The method of claim 10, wherein said compound is selected from the group consisting of adenylate cyclase toxin, forskolin, and L-858051.

12. The method of claim 9, wherein said agent is a compound which inhibits a phosphodiesterase.

13. The method of claim 12, wherein said compound is selected from the group consisting of RO 20-1724, Rolipram, Etazolate, and 3-isobutyl-1-methylxanthine.

14. The method of claim 2, wherein said RAR agonist is a RARα agonist selected from the group consisting of 9-cis retinoic acid, all-trans retinoic acid, (4-[[(2,3-Dihydro-1,1,3,3-tetramethyl-2-oxo-1H-inden-5-yl)carbonyl]amino]benzoic acid), AM-80 and AM-580.

15. The method of claim 3, wherein said cytokine is selected from the group consisting of a granulocyte colony-stimulating factor (G-CSF), granulocyte macrophage colony-stimulating factor (GM-CSF) and macrophage colony-stimulating factor (M-CSF).

16. The method of claim 1, wherein said retinoid X receptor (RXR)-selective agonist is a compound of Formula I:

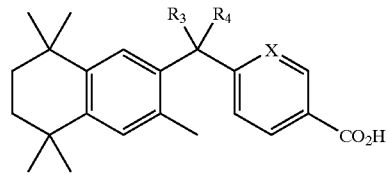

or a pharmaceutically acceptable salt thereof, wherein:
$R_3$, $R_4$ is —$CH_2CH_2$— or —$CH_2O$—; and
X is CH or N, provided that if X is N, then $R_3$, $R_4$ is —$CH_2CH_2$—.

17. The method of claim 1, wherein said retinoid X receptor (RXR)-selective agonist is a compound of Formula II:

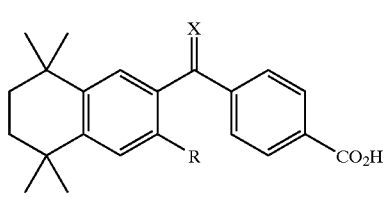

or a pharmaceutically acceptable salt thereof, wherein:
R is hydrogen, methyl, ethyl, isopropyl, fluorine, chlorine, or bromine; and
X is O or $CH_2$.

18. The method of claim 1, wherein said retinoid X receptor (RXR)-selective agonist is a compound of Formula III:

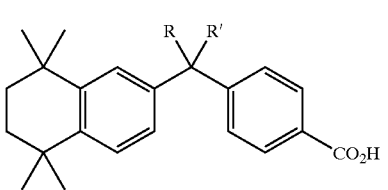

or a pharmaceutically acceptable salt thereof, wherein:
R, R' is —$SCH_2CH_2CH_2S$—, —$(CH_3)_2C$—, —$SCH_2CH_2S$—, —$OCH_2CH_2S$—, —$OCH_2CH_2O$—, or —$OCH_2CH_2O$—.

19. A method of treating breast cancer in a subject, said method comprising:
   (a) administering to said subject a pharmaceutically effective amount of a retinoid X receptor (RXR)-selective agonist; and
   (b) administering to said subject a pharmaceutically effective amount of an agent which is capable of activating protein kinase A (PKA).

20. The method of claim 19, further comprising (c) administering to said subject a pharmaceutically effective amount of a retinoic acid receptor agonist (RAR).

21. The method of claim 19, further comprising administering to said subject a pharmaceutically effective amount of a cytokine selected from the group consisting of a granulocyte colony-stimulating factor (G-CSF), a granulocyte macrophage colony-stimulating factor (GM-CSF), a macrophage colony-stimulating factor (M-CSF), interleukin 8 (L-8), monocyte chemoattractant protein 1 (MCP1), macrophage inflammatory protein MIP1α, and macrophage inflammatory protein MIP1 β.

22. The method of claim 19, wherein said RXR-s elective agonist is selected from the group consisting of 9-cis retinoic acid, bexarotene, 4-[1-[5,6-Dihydro-3,5,5-trimethyl-8-(1-methylethyl)-2-naphthalenyl]ethenyl]benzoic acid, and SR11237.

23. The method of claim 19, wherein said agent is selected from the group consisting of a PKA agonist, a compound which increases cAMP level, and a compound which inhibits a phosphodiesterase.

24. The method of claim 23, wherein said PKA agonist is selected from the group consisting of 8-bromo-cAMP, Sp-cAMPS, 8CPT-cAMP, dibutyryl-cAMP, Sp-5,6-DCl-cBiMPS, adenylate cyclase toxin, forskolin, L-858051, and Sp-8-pCPT-cGMPS, and said compound which increases cAMP level is selected from the group consisting of adenylate cyclase toxin, forskolin, and L-858051, and said compound which inhibits a phosphodiesterase is selected from the group consisting of RO 20-1724, Rolipram, Etazolate, and 3-isobutyl-1-methylxanthine.

25. The method of claim 20, wherein said RAR agonist is a RARα agonist selected from the group consisting of 9-cis retinoic acid, all-trans retinoic acid, (4-[[(2,3-Dihydro-1,1,3,3-tetramethyl-2-oxo-1H-inden-5-yl)carbonyl]amino] benzoic acid), AM-80 and AM-580.

26. The method of claim 21, wherein said cytokine is selected from the group consisting of a granulocyte colony-stimulating factor (GCSF), granulocyte macrophage colony-stimulating factor (GM-CSF) and macrophage colony-stimulating factor (M-CSF).

27. The method of claim 19, wherein said retinoid X receptor (RXR)-selective agonist is selected from the group consisting of a compound of Formula I:

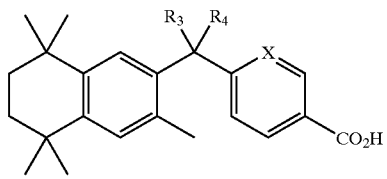

or a pharmaceutically acceptable salt thereof, wherein:

$R_3$, $R_4$, is —$CH_2CH_2$— or —$CH_2O$—; and

X is CH or N, provided that if X is N, then $R_3$, $R_4$ is —$CH_2CH_2$—;

a compound of Formula II

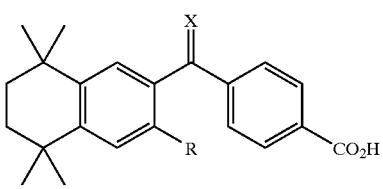

or a pharmaceutically acceptable salt thereof, wherein:

R is hydrogen, methyl, ethyl, isopropyl, fluorine, chlorine, or bromine; and

X is O or $CH_2$; and a compound of Formula III

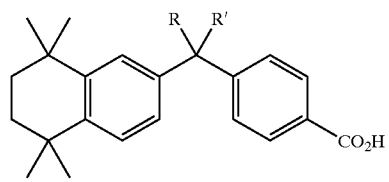

or a pharmaceutically acceptable salt thereof, wherein:

R, R' is —$SCH_2CH_2CH_2S$—, —$(CH_3)_2C$—, —$SCH_2CH_2S$—, —$OCH_2CH_2S$—, —$OCH_2CH_2O$—, or —$OCH_2CH_2O$—.

28. A method of inhibiting proliferation or increasing differentiation of leukemia or breast cancer cells, said method comprising:

(a) administering to said cells an effective amount of a retinoid X receptor (RXR)-selective agonist; and (b) administering to said cells an effective amount of an agent which is capable of activating protein kinase A (PKA).

29. The method of claim 24, further comprising (c) administering to said cells an effective amount of a retinoic acid receptor agonist (RAR).

30. The method of claim 28, further comprising administering to said cells an effective amount of a cytokine selected from the group consisting of a granulocyte colony-stimulating factor (G-CSF), a granulocyte macrophage colony-stimulating factor (GM-CSF), a macrophage colony-stimulating factor (M-CSF), interleukin 8 (IL-8), monocyte chemoattractant protein 1 (MCP1), macrophage inflammnatory protein MIP1α, and macrophage inflammatory protein MIP1β.

31. The method of claim 28, wherein said RXR-selective agonist is selected from the group consisting of 9-cis retinoic acid, bexarotene, 4-[1-[5,6-Dihydro-3,5,5-trimethyl-8-(1-methylethyl)-2-naphthalenyl]ethenyllbenzoic acid, and SR 11237.

32. The method of claim 28, wherein said agent is selected from the group consisting of a PKA agonist, a compound which increases cAMP level, and a compound which inhibits a phosphodiesterase.

33. The method of claim 32, wherein said PKA agonist is selected from the group consisting of 8-bromo-cAMP, Sp-cAMPS, 8CPT-cAMP, dibutyryl-cAMP, Sp-5,6-DCl-cBiMPS, adenylate cyclase toxin, forskolin, L-858051, and Sp-8-pCPT-cGMP, and said compound which increases cAMP level is selected from the group consisting of adenylate cyclase toxin, forskolin, and L-858051, and said compound which inhibits a phosphodiesterase is selected from the group consisting of RO 20-1724, Rolipram, Etazolate, and 3-isobutyl-1-methylxanthine.

34. The method of claim 29, wherein said RAR agonist is a RARα agonist selected from the group consisting of 9-cis retinoic acid, all-trans retinoic acid, (4-[[(2,3-Dihydro-1,1,3,3-tetramethyl-2-oxo-1H-inden-5-yl)carbonyl] aminolbenzoic acid), AM-80 and AM-580.

35. The method of claim 30, wherein said cytokine is selected from the group consisting of a granulocyte colony-stimulating factor (G-CSF), granulocyte macrophage colony-stimulating factor (GM-CSF) and macrophage colony-stimulating factor (M-CSF).

36. The method of claim 28, wherein said retinoid X receptor (RXR)-selective agonist is selected from the group consisting of a compound of Formula I:

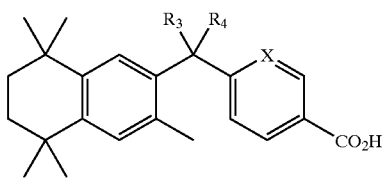

I or a pharmaceutically acceptable salt thereof, wherein:

$R_3$, $R_4$ is —$CH_2CH_2$— or —$CH_2O$—; and

X is CH or N, provided that if X is N, then $R_3$, $R_4$ is —$CH_2CH_2$—;

a compound of Formula II:

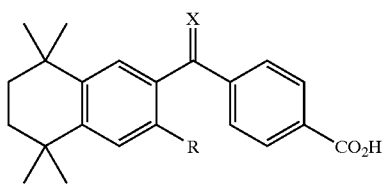

II or a pharmaceutically acceptable salt thereof, wherein:

R is hydrogen, methyl, ethyl, isopropyl, fluorine, chlorine, or bromine; and

X is O or $CH_2$; and a compound of Formula III:

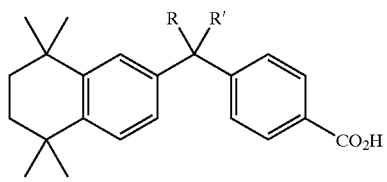

III or a pharmaceutically acceptable salt thereof, wherein:

R, R' is —$SCH_2CH_2CH_2S$—, —$(CH_3)_2C$—, —$SCH_2CH_2S$—, —$OCH_2CH_2S$—, —$OCH_2CH_2O$—, or —$OCH_2CH_2O$—.

37. The method of claim 28, wherein said cells are leukemia cells.

38. The method of claim 28, wherein said cells are breast cancer cells.

39. The method of claim 37, wherein said leukemia cells are acute promyelocytic leukemia (APL) cells.

\* \* \* \* \*

UNITED STATES PATENT AND TRADEMARK OFFICE
CERTIFICATE OF CORRECTION

PATENT NO. : 6,624,154 B1
DATED : September 23, 2003
INVENTOR(S) : Benoit et al.

It is certified that error appears in the above-identified patent and that said Letters Patent is hereby corrected as shown below:

Title page,
Item [75], Inventors, please delete "Monrsouir" and insert therein -- Montsoult --.
Item [56], References Cited, U.S. PATENT DOCUMENTS, please insert -- 5,399,586 3/1995 Davies et al. --; please insert -- 5,780,676 7/1998 Boehm *et al.* --
FOREIGN PATENT DOCUMENTS, please insert -- WO 93/21146 10/1993 WIP0 -- please insert -- CA 2,230,637 3/1997 Canada --; and please -- insert -- WO 99/06036 2/1999 WIPO --.
OTHER PUBLICATIONS please insert -- Beard, R.L., *et al.*, "Structural Basis for the Differential RXR and RAR Activity of Stilbene Retinoid Analogs," *Bioorg. Med. Chem. Lett. 4*:1447 1452, Elsevier Science Ltd (1994). --;
please insert -- Beard, R.L., *et al.*, "Synthesis and Structure-Activity Relationships of Stilbene Retinoid Analogs Substituted with Heteroaromatic Carboxylic Acids," *J. Med. Chem. 38*:2820-2829, American Chemical Society (1995). --;
please insert -- Beard, R.L., *et al.*, "Synthesis and Structure-Activity Relationships of Retinoid X Receptor Selective Diaryl Sulfide Analogs of Retinoic Acid," *J. Med. Chem. 39*:3556-3563, American Chemical Society (1996). --;
please insert -- Davies, P.J.A., *et al.*, "Retinoid-Regulated Gene Expression in Normal and Leukemic Myeloid Cells," *BioEssays* 1:160-165, John Wiley & Sons, Inc. (1984). --;
please insert -- Davies, P.J.A., *et al.*, "Retinoic Acid-induced Expression of Tissue Transglutaminase in Human Promyelocytic Leukemia (HL-60) Cells," *J. Biol. Chem.* 260:5166-5174, The American Society of Biological Chemists, Inc. (1985). --;
please insert -- Davies, P.J.A., *et al.*, "Retinoid-regulated expression of transglutaminases: links to the biochemistry of programmed cell death," in *Retinoids in Normal Development and Teratogenesis,* Morriss-Kay, G., ed., Oxford University Press, New York, pp. 249-263 (1992). --;
please insert -- Fontana, J.A., *et al.*, "Inhibition of Human Mammary Carcinoma Cell Proliferation by Retinoids and Intracellular cAMP-Elevating Compounds," *JNCI* 78:1107-1112, National Cancer Institute (1987). --;
please insert -- Huggenvik, J.I., *et al.*, "Modification of the Retinoic Acid Signaling Pathway by the Catalytic Subunit of Protein Kinase-A," *Mol. Endo.* 7:543-550, The Endocrine Society (1993) --;
please insert -- Moore, W.T., *et al.*, "Retinoic Acid-induced Expression of Tissue, Transglutaminase in Mouse Peritoneal Macrophages," *J. Biol. Chem.* 259:12794-12802, The American Society of Biological Chemists, Inc. (1984). --;
please insert -- Murtaugh, M.P., *et al.*, "Cyclic AMP Potentiates the RetinoicAcid-induced Expression of Tissue Transglutaminase in Peritoneal Macrophages,"'*J Biol. Chem.* 261:614-621, The American Society of Biological Chemists, Inc. (1986). --;
please insert -- Nadzan, A.M., *et al.*, "Design of Novel RXR Selective Retinoids," *Euro. J Med. Chem.* 30:519s-533s, Elsevier Science Ltd (1995). --;
please insert -- Nagy, L., *et al.*, "Retinoid-Regulated Expression of BCL-2 and Tissue Transglutaminase During the Differentiation and Apoptosis of Human Myeloid Leukemia (HL-60) Cells," *Leukemia Res.* 20:499-505, Elsevier Science Ltd (1996). --;

UNITED STATES PATENT AND TRADEMARK OFFICE
CERTIFICATE OF CORRECTION

PATENT NO. : 6,624,154 B1
DATED : September 23, 2003
INVENTOR(S) : Benoit et al.

It is certified that error appears in the above-identified patent and that said Letters Patent is hereby corrected as shown below:

Title page (cont'd),
please insert -- Nagy, L., *et al.*, "Retinoid-induced apoptosis in normal and neoplastic tissues," *Cell Death and Differentiation* 5:11-19, Stockton Press (January 1998). --;
please insert -- Lopez-Boado, *et al.*, "Retinoic acid-induced expression of apolipoprotein D and concomitant growth arrest in human breast cancer cells are mediated through a retinoic acid receptor RAR alpha-dependent signaling pathway," *J. Biol. Chem. 271*:32105-32111, American Society for Biochemistry and Molecular Biology (1996). --.

Column 43,
Line 30, please delete "a" and insert therein -- $\alpha$ --.

Column 44,
Line 47, please delete "—$OCH_2CH_2O$—" and insert therein -- —$OCH_2CH_2CH_2O$— --.
Line 67, please delete "(L-8)" and insert therein -- (IL-8) --

Column 46,
Line 14, please delete "—$OCH_2CH_2O$—" and insert therein -- —$OCH_2CH_2CH_2O$— --.
Line 26, please delete " 24" and insert therein -- 28 --
Lines 35-36, please delete "inflammnatory" and insert therein -- inflammatory --.
Line 41, please delete "ethenyllbenzoic" and insert therein -- ethenyl]benzoic --.
Line 62, please delete "aminolbenzoic" and insert therein -- amino]benzoic --.

Column 48,
Line 21, please delete "—$OCH_2CH_2O$—" and insert therein -- —$OCH_2CH_2CH_2O$— --.

Signed and Sealed this

Twenty-seventh Day of July, 2004

JON W. DUDAS
*Acting Director of the United States Patent and Trademark Office*